(12) United States Patent
Inouye et al.

(10) Patent No.: US 7,985,575 B2
(45) Date of Patent: Jul. 26, 2011

(54) SINGLE PROTEIN PRODUCTION IN LIVING CELLS FACILITATED BY A MESSENGER RNA INTERFERASE

(75) Inventors: Masayori Inouye, New Brunswick, NJ (US); Junjie Zhang, Beijing (CN); Motoo Suzuki, Kagawa-Ken (JP)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 989 days.

(21) Appl. No.: 11/750,314

(22) Filed: May 17, 2007
(Under 37 CFR 1.47)

(65) Prior Publication Data
US 2010/0035346 A1   Feb. 11, 2010

Related U.S. Application Data

(63) Continuation-in-part of application No. 11/660,820, filed as application No. PCT/US2005/040107 on Nov. 4, 2005, now abandoned.

(60) Provisional application No. 60/624,976, filed on Nov. 4, 2004, provisional application No. 60/801,168, filed on May 17, 2006.

(51) Int. Cl.
*C12N 1/21* (2006.01)

(52) U.S. Cl. ................................ 435/252.33; 435/320.1

(58) Field of Classification Search ........................ None
See application file for complete search history.

(56) References Cited

U.S. PATENT DOCUMENTS

| | | | |
|---|---|---|---|
| 5,187,083 A | 2/1993 | Mullis |
| 5,234,824 A | 8/1993 | Mullis |
| 5,333,675 A | 8/1994 | Mullis et al. |
| 5,656,493 A | 8/1997 | Mullis et al. |
| 2004/0018571 A1 | 1/2004 | Reiter et al. |

OTHER PUBLICATIONS

Elenberg-Kulka and Gerdes, "Addiction Modules and Programmed Cell Death and Anti-Death in Bacterial Cultures," Ann. Rev. Microbiol., vol. 53, pp. 43-70 (1999).
Engelberg-Kulka et al., "Bacterial Programmed Celled Death Systems as Targets for Antibiotics," Trends Microbiol., vol. 12, p. 66-71n (2004).
Christiansen et al., Toxin-Antitoxin Loci as Stress-response-elements: ChpAK/MazF and ChpBK Cleave Translated RNAs and are Counteracted by tmRNA, J. Mol. Biol., vol. 332, pp. 809-819 (2003).
Kamada et al., "Crystal Structure of the MazE/MazF Complex: Molecular Bases of Antidote-Toxin Recognition," Mol. Cell, vol. 11, pp. 875-884 (2003).
Zhang et al., "Characterization of the Interactions within the MazEF Addiction Molecule of *Escherichia coli*," J. Biol. Chem., vol. 278, pp. 32300-32306 (2003).
Zhang et al., "Interference of mRNA function by sequence-specific Endoribonuclease PemK," J. Biol. Chem., vol. 279, pp. 20678-20684 (2004).
J. Sambrook and D. W. Russell, "Molecular Cloning: A Laboratory Manual, Third Edition, Chapter 15.12," Cold Spring Harbor Press, Cold Spring Harbor, New York, (2001).
Konigsbert et al., "Evidence for Use of Rare Codons in the dnaG gene and Other Regulatory Genes of *Escherichia coli*," Proc. Nat'l Acad. Sci. U.S.A., vol. 80, pp. 687-691 (1983).
Thieringer et al., "Cold Shock and Adaptation," Bioessays, vol. 20(1), pp. 49-57 (1998).
Qing et al., "Cold-shock Induced High-Yield Protein Production in *Escherichia coli*," Nat. Biotechnol., vol. 22(7), pp. 877-882 (2004).
Tokuda and Matsuyama, "Sorting of Lipoproteins to the Outer Membranes in *E. coli*," Biochem. Biophys. Acta., vol. 1693, pp. 5-13 (2004).
Yamaguchi et al., "A Single Amino Acid Determinant of the Membrane Localization of Lipoproteins," Cell, vol. 53(3), pp. 423-432 (1988).
Wolfe et al., "The Isolation of Homogenous Leader Peptidase from a Strain of *Escherichia coli* Which Overproduces the Enzyme," J. Biol. Chem., vol. 257(13), pp. 7898-7902 (1982).
Pedersen et al., "Rapid Induction and Reversal of a Bacteriostatic Condition by Controlled Expression of Toxins and Antitoxins," Mol. Microbiol., vol. 45(2), pp. 501-510 (2002).
Amitai et al., "MazF-Mediated Cell Death in *Escherichia coli*: A Point of No Return," J. Bacteriol., vol. 186(24), pp. 8295-8300 (2004).
M. Suzuki et al., "Single Protein Production in Living Cells Facilitated by an mRNA Interferase," Mol. Cell., vol. 18, pp. 253-261 (2005).
Zhang et al., "MazF Cleaves Cellular mRNAs Specifically at ACA to Block Protein Synthesis in *Escherichia coli*," Mol. Cell., vol. 12, pp. 913-923 (2003).
W.A. Hendrickson, "Synchrotron Crystallography," Trends Biochem. Sci., vol. 25, pp. 637-643 (2000).
J. J. Bellizzi et al., "Producing Selenomethionine-Labeled Proteins With a Baculovirus Expression Vector System," Structure, vol. 7(11), pp. R263-R267 (1999).

(Continued)

*Primary Examiner* — James S Ketter
(74) *Attorney, Agent, or Firm* — Lowenstein Sandler PC

(57) ABSTRACT

The present invention describes a single-protein production (SPP) system in living *E. coli* cells that exploits the unique properties of an mRNA interferase, for example, MazF, a bacterial toxin that is a single stranded RNA- and ACA-specific endoribonuclease, which efficiently and selectively degrades all cellular mRNAs in vivo, resulting in a precipitous drop in total protein synthesis. Concomitant expression of MazF and a target gene engineered to encode an ACA-less mRNA results in sustained and high-level (up to 90%) target expression in the virtual absence of background cellular protein synthesis. Remarkably, target synthesis continues for at least 4 days, indicating that cells retain transcriptional and translational competence despite their growth arrest. SPP technology works well for yeast and human proteins, even a bacterial integral membrane protein. This novel system enables unparalleled signal to noise ratios that should dramatically simplify structural and functional studies of previously intractable but biologically important proteins. The present invention also provides an optimized condensed single protein production system.

7 Claims, 22 Drawing Sheets

OTHER PUBLICATIONS

W. A. Hendrickson, et al., "Selenomethionyl Proteins Produced for Analysis by Multiwavelength Anomalous Diffraction (MAD): A Vehicle for Direct Determination of Three-Dimensional Structure," Embo J, vol. 9(5), pp. 1665-1672 (1990).

T. Kigawa et al., "Selenomethionine Incorporation Into a Protein by Cell-Free Synthesis," J. Struct. Funct. Genomics, vol. 2, pp. 29-35 (2001).

R. B. Bourret et al., "Activation of the Phosphosignaling Protein CheY. II. Analysis of Mutants by 19F NMR and Protein Engineering," J. Biol. Chem., vol. 268(18), pp. 13089-13096 (1993).

S. K. Drake et al, "Activation of the Phosphosignaling Protein CheY. I. Analysis of the Phosphorylated Conformation by 19F NMR and Protein Engineering," J. Biol. Chem., vol. 268(18), pp. 13081-13088 (1993).

J. Tian et al, "Accurate Multiplex Gene Synthesis from Programmable DNA Microchips," Nature, vol. 432, pp. 1050-1054 (2004).

M. M. Dedmon et al., "FlgM Gains Structure in Living Cells," Proc. Nat'l Acad. Sci. U.S.A., vol. 99, pp. 12681-12684 (2002).

Z. Serber et al., "High-Resolution Macromolecular NMR Spectroscopy Inside Living Cells," J. Am. Chem. Soc., vol. 123, pp. 2446-2447 (2001).

Z. Serber et al., "Evaluation of Parameters Critical to Observing Proteins Inside Living *Escherichia coli* by In-Cell NMR Spectroscopy," J. Am. Chem. Soc., vol. 123(37), pp. 8895-8901 (2001).

Zhang, Y., et al.; "Characterization of ChpBK, an mRNA Interferase from *Escherichi coli*;" The Journal of Biological Chemistry; vol. 28; No. 28; Jul. 15, 2005; p. 26080-26088.

Zhu, L., et al.; "Characterization of mRNA Interferases from Mycobacterium Tuberculosis;" The Journal of Biological Chemistry; vol. 281; No. 27; Jul. 7, 2006; p. 18638-18643.

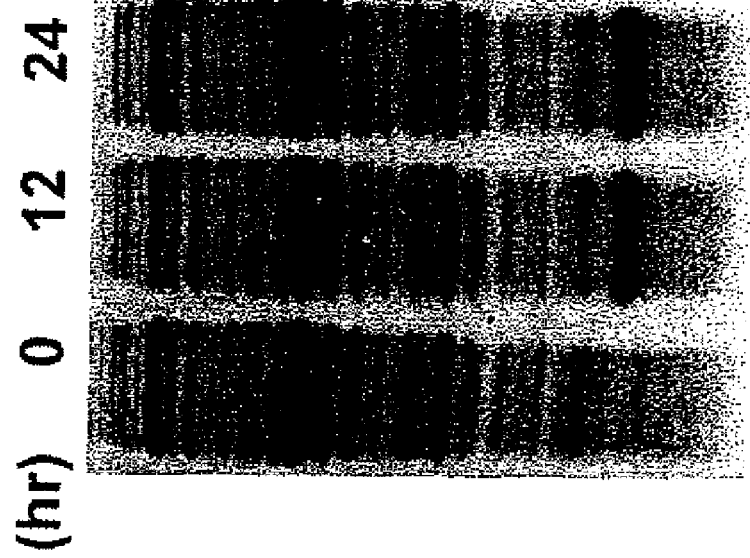

Fig. 2A

| translation enhancing element | His₆ | factor Xa site | NdeI site |

```
  M   N   H   K   V   H   H   H   H   H   H   I   E   G   R   H   M   G   P   A
 AUG AAU CAU AAA GUG CAU CAU CAU CAU CAU CAU AUC GAA GGU AGG CAT ATG GGU
 CCA GCA

S   V   P   T   T   C   C   F   N   L   A   N   R   K   I   P   L   Q   R   L
 UCU GUU CCG ACU ACC UGU UGC UUU AAC CUG GCG AAC CGC AAA AUU CCG CUG
 CAG CGC CUG

E   S   Y   R   R   I   T   S   G   K   C   P   Q   K   A   V   I   F   K   T
 GAA AGC UAU CGC CGU AUU ACC UCU GGC AAA UGC CCG CAG AAA GCG GUG AUC
 UUU AAA ACC

K   L   A   K   D   I   C   A   D   P   K   K   K   W   V   Q   D   S   M   K
 AAA CUG GCG AAA GAU AUU UGC GCG GAU CCG AAA AAA AAA UGG GUG CAG GAU
 UCU AUG AAA

Y   L   D   Q   K   S   P   T   P   K   P     SEQ ID NO.: 3
 UAU CUG GAU CAG AAA UCU CCG ACC CCG AAA CCG UAA     SEQ ID NO.: 1
```

Fig. 3A

```
M  V  S  R  Y  V  P  D  M  G  D  L  I  W  V  D  F  D  P  T
AUG GUA AGC CGA UAC GUA CCC GAU AUG GGC GAU CUG AUU UGG GUU GAU UUU
GAC CCG ACC
K  G  S  E  Q  A  G  H  R  P  A  V  V  L  S  P  F  M  Y  N
AAA GGU AGC GAG CAA GCU GGC CAU CGU CCA GCU GUU GUC CUG AGU CCU UUC
AUG UAU AAU
N  K  T  G  M  C  L  C  V  P  C  T  T  Q  S  K  G  Y  P  F
AAU AAA ACC GGU AUG UGU CUG UGU CCU UGU ACG ACG CAA UCA AAA GGA
UAU CCG UUC
E  V  V  L  S  G  Q  E  R  D  G  V  A  L  A  D  Q  V  K  S
GAA GUU GUU UUA UCC GGU CAG GAA CGU GAU GGC GUA GCG UUA GCU GAU CAG
GUA AAA AGU
I  A  W  R  A  R  G  A  T  K  K  G  T  V  A  P  E  E  L  Q
AUC GCC UGG CGG GCA AGA GGA GCA ACG AAG AAA GGA ACC GUU GCC CCA GAG
GAA CUG CAA
L  I  K  A  K  I  N  V  L  I  G   SEQ ID NO.: 4
CUC AUU AAA GCC AAA AUU AAC GUA CUG AUU GGG UAG   SEQ ID NO.: 2
```

(U)

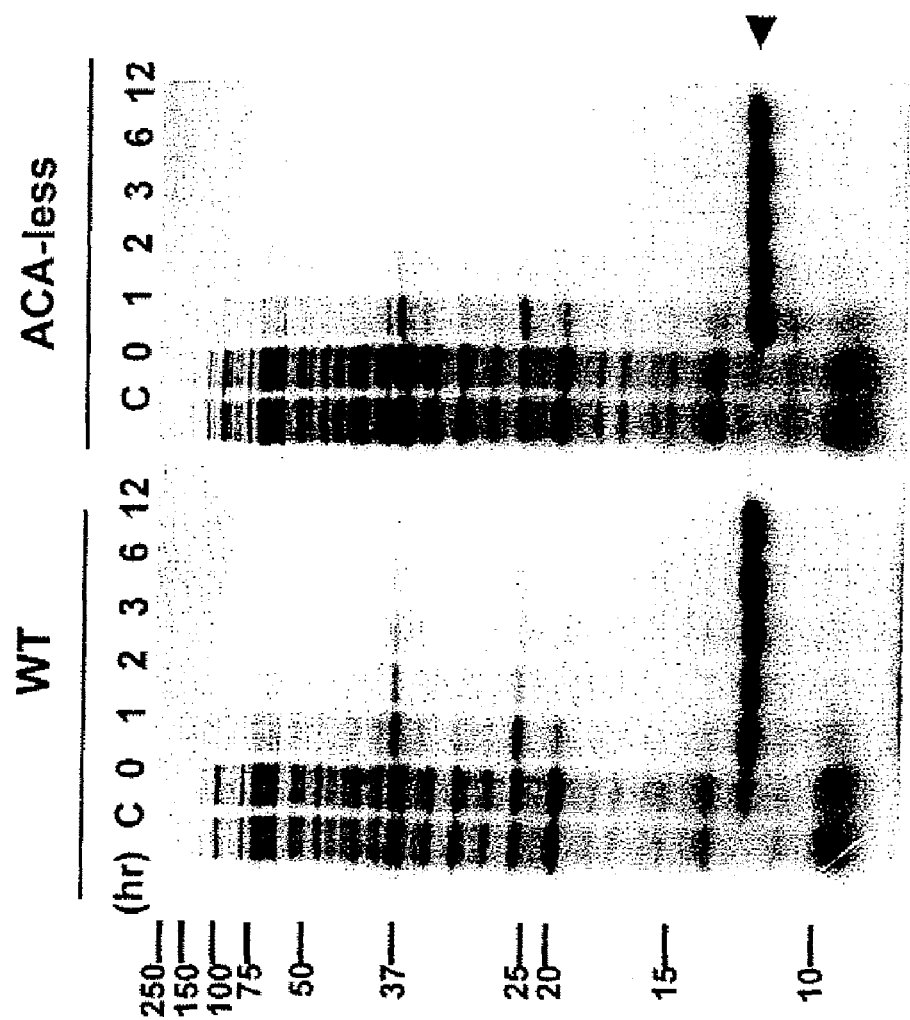

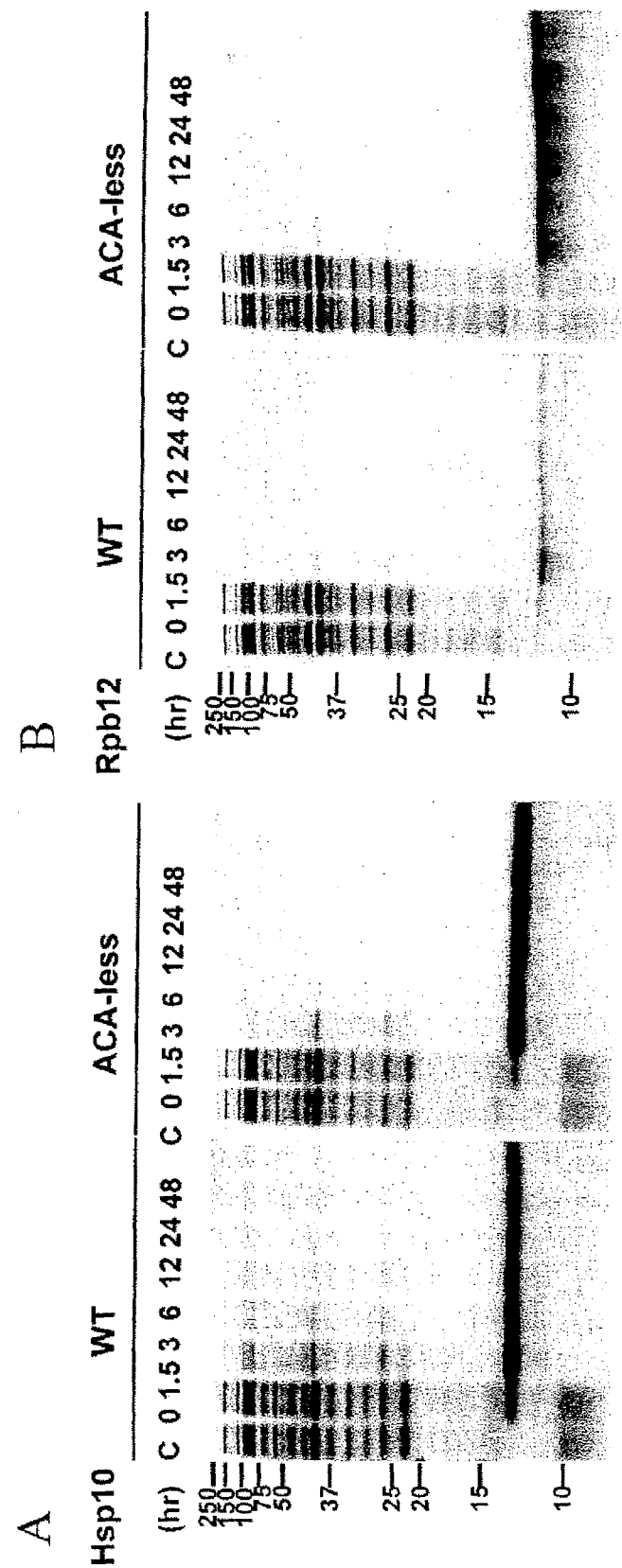

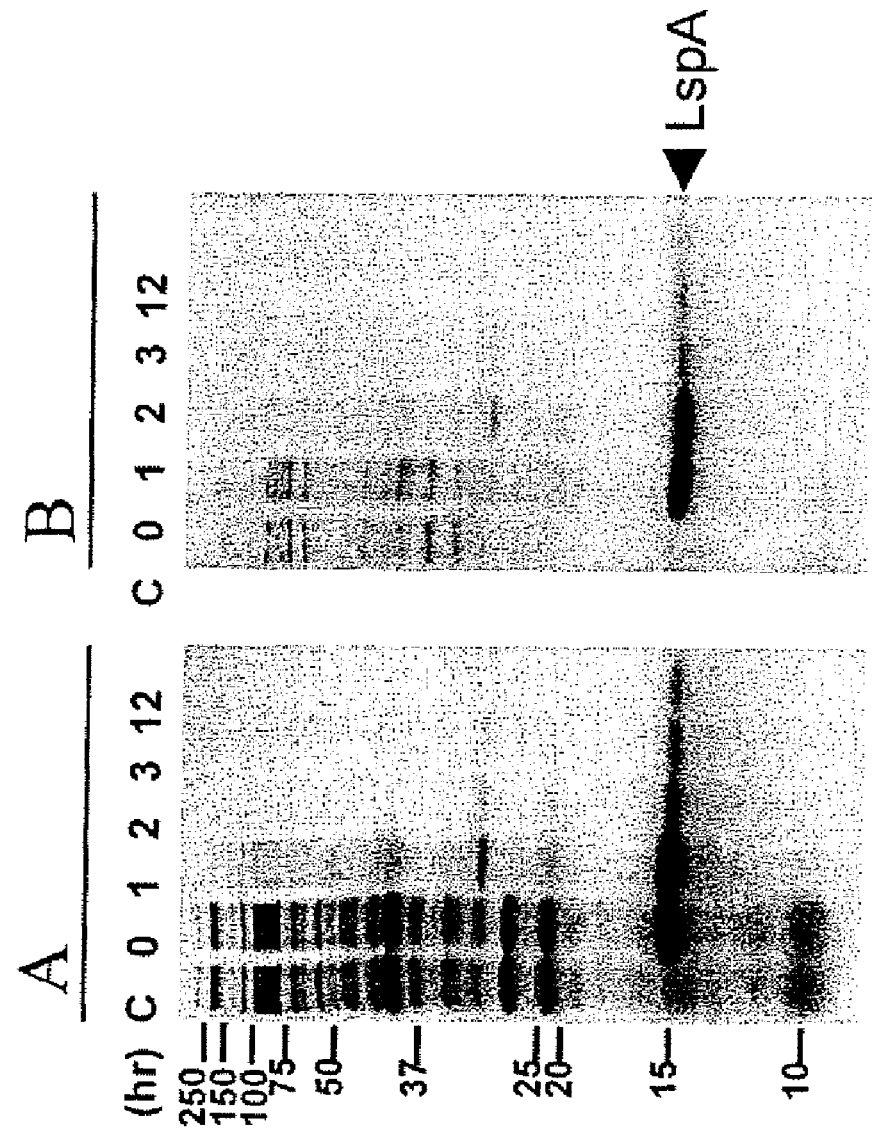

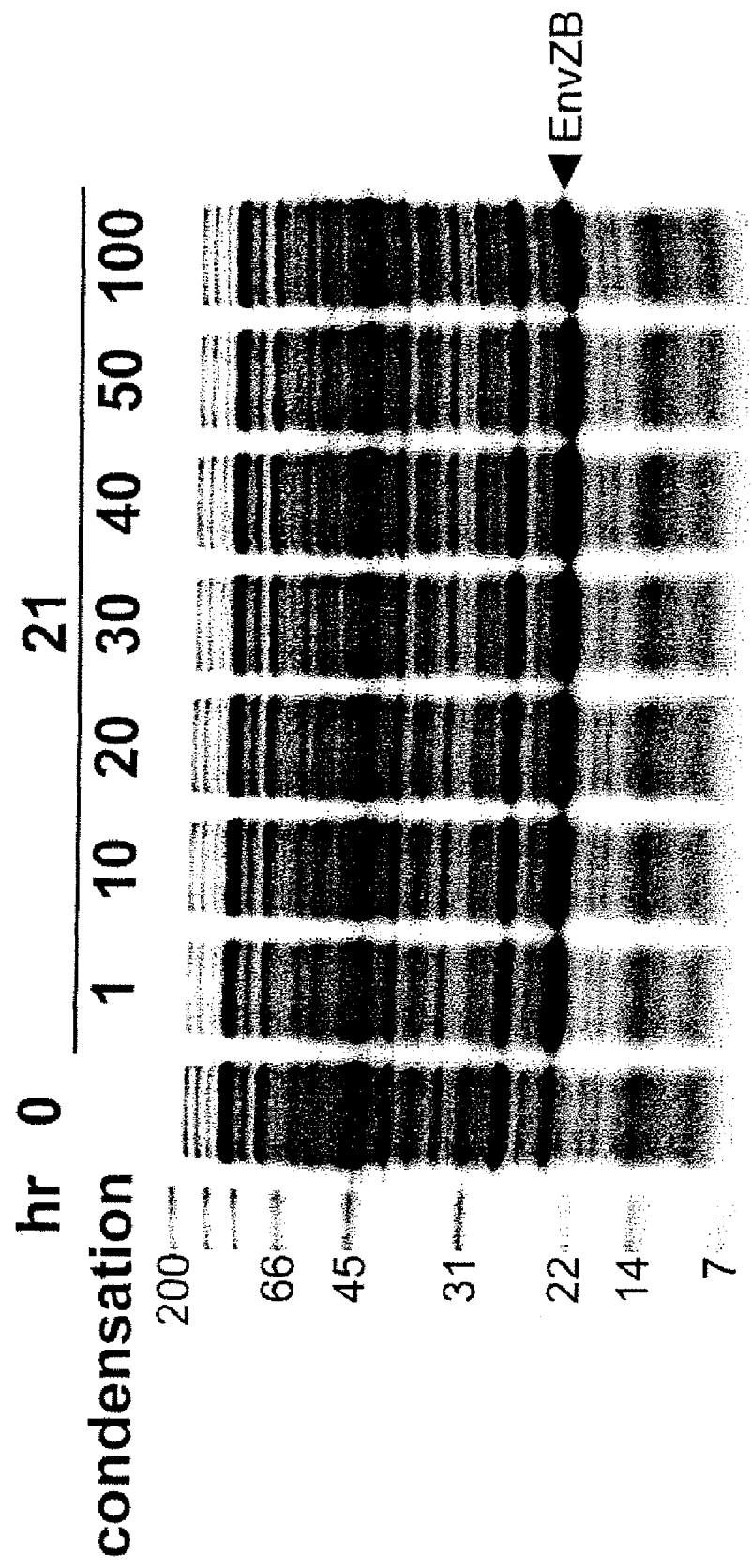

SINGLE PROTEIN PRODUCTION IN LIVING CELLS FACILITATED BY A MESSENGER RNA INTERFERASE

CROSS-REFERENCE TO ELATED APPLICATIONS

This application is a continuation-in-part of U.S. patent application Ser. No. 11/660,820, fled Feb. 21, 2007 now abandoned, entitled "Single Protein Production in Living Cells Facilitated by a Messenger RNA Interferase," which is a U.S. national stage application of International Patent Application No. PCT/US2005/040107, filed Nov. 4, 2005, which claims priority to U.S. Provisional Application No. 60/624,976, filed Nov. 4, 2004, entitled "Single Protein in Living Cells Facilitated by an mRNA Interferase," by Inouye et al., the disclosures of all of which are incorporated herein by reference in their entirety. This application also claims priority to U.S. Provisional Application No. 60/801,168, filed May 17, 2006, entitled "Bacterial Bioreactors for Economical High Yield Protein Production," by Inouye et al., filed May 17, 2006, the disclosure of which is incorporated herein by reference in its entirety.

FIELD OF THE INVENTION

The present invention relates to a system for producing a single protein in living cells facilitated by an mRNA interferase that is a single-stranded RNA- and sequence-specific endoribonuclease.

STATEMENT UNDER 37 C.F.R. §1.821(f)

In accordance with 37 C.F.R. §1.821(f), the content of the attached Sequence Listing and the attached computer readable copy of the Sequence Listing submitted in the parent application, U.S. Ser. No. 11/660,820, filed Feb. 21, 2007, are identical.

BACKGROUND OF THE INVENTION

Most bacteria contain suicidal genes whose expression leads to growth arrest and eventual death upon exposure to cellular stress (reviewed by Elenberg-Kulka and Gerdes, Ann. Rev. Microbiol. 53: 43-70 (1999); Engelberg-Kulka et al., Trends Microbiol. 12: 66-71 (2004)). These toxin genes are usually co-expressed with their cognate antitoxin genes in the same operon (referred to as an addiction module or anti-toxin-toxin system). E. coli has five addiction modules (Christensen et al., J. Mol. Biol. 332: 809-19 (2003)) among which the MazE/MazF module has been most extensively investigated. The x-ray structure of the MazE/MazF complex (Kamada et al., Mol. Cell. 11: 875-84 (2003)) is known and the enzymatic activity of MazF has been recently characterized (Zhang et al, J. Biol. Chem. 278: 32300-306 (2003)).

MazF is a sequence-specific endoribonuclease that specifically cleaves single-stranded RNAs (ssRNAs) at ACA sequences. An endonuclease is one of a large group of enzymes that cleave nucleic acids at positions within a nucleic acid chain. Endoribonucleases or ribonucleases are specific for RNA. MazF is referred to as an mRNA interferase since its primary target is messenger RNA (mRNA) in vivo. Transfer RNAs (tRNAs) and ribosomal RNAs (rRNAs) appear to be protected from cleavage because of either their secondary structure or association with ribosomal proteins, respectively. Therefore, MazF expression causes nearly complete degradation of mRNA, leading to severe reduction of protein synthesis and ultimately, to cell death (Zhang et al., Mol. Cell. 12: 913-23 (2003)). MazF is found in selected bacteria, and recently the E. coli protein PemK (encoded by plasmid R100) was also shown to be a sequence-specific endoribonuclease (Zhang et al., J. Biol. Chem. 279: 20678-20684 (2004)). PemK cleaves RNA with high specificity at a specific nucleic acid sequence, i.e., UAX, wherein X is C, A or U. See PCT/US2004/018571, which is incorporated herein by reference. These sequence-specific endoribonucleases are conserved, underscoring their essential roles in physiology and evolution. We refer to this family of sequence-specific endoribonuclease toxins as "mRNA interferases" (Zhang et al., J. Biol. Chem. 279: 20678-20684 (2004)).

In the present study, we have exploited the unique cleavage properties of MazF to design a single-protein production (SPP) system in living E. coli cells. Upon expression of a gene engineered to express an ACA-less mRNA without altering its amino acid sequence, high levels of individual target protein synthesis were sustained for at least for 96 hours while background cellular protein synthesis was virtually absent. Therefore, the toxic effect of MazF is directed at mRNA with minimal side effects on cellular physiology. In fact, despite their state of growth arrest, these cells retain essential metabolic and biosynthetic activities for energy metabolism (ATP production), amino acid and nucleotide biosynthesis and transcription and translation. In addition to demonstrating the efficacy of the SPP system for human and yeast proteins, the technology was also effective for overexpression of an integral inner membrane protein whose natural levels of expression are relatively low. The SPP system yields unprecedented signal to noise ratios that both preclude any protein purification steps for experiments that require recovery of proteins in isolation, and, more importantly, enable structural and functional studies of proteins in intact, living cells.

This bacterial single protein production (SPP) system supports high yield recombinant protein production in the virtual absence of background cellular protein synthesis. This high signal to noise ratio is facilitated by coexpression of an endoribonuclease that specifically cleaves ACA sequences of mRNAs (resulting in global mRNA degradation and translation inhibition) along with an ACA-less target gene (whose mRNA is uncleavable so its translation is undeterred). Now we have optimized the expression vectors and growth conditions to tailor this bacterial bioreactor technology toward highly economical protein production for structure determination by NMR and X-ray crystallography. We also demonstrate that exponentially growing cultures could be condensed 40-fold (cSPP) without affecting final protein yields and support very high incorporation of selenomethionine and fluorophenylalanine without cytotoxicity. cSPP also resulted in a substantial reduction in the cost of sample labeling, to only 2.5% that of conventionally prepared samples. This major cost efficiency, coupled with the absence of cytotoxicity upon robust protein expression, imparts advantages to the cSPP system that are especially well suited to the structural genomics mission and other large scale protein expression applications.

Mature eotaxin (A) or HR91(B) and EnvZV (C) were expressed from pColdI(SP-2) (1 ACA in 3'-UTR) or pColdI (SP-4) (No ACA in 3'-UTR) along with MazF from pACY-CmazF. Upon reaching an $OD_{600}$ of 0.5, cultures were shifted from 37° C. to 15° C. for 45 min. New protein synthesis was then monitored by isotopic labeling with [$^{35}$S]-mertionine for 15 min before (C control lane) or at intervals after IPTG induction for up to seven days. Equivalent amounts of cell lysate, derived from equal culture volumes, were subjected to SDS-PAGE followed by autoradiography. New protein synthesis from HR969 expressing cells was monitored for the hrs designated after IPTG induction as described in A-C (D); accumulated total cellular protein derived from the unlabeled samples otherwise subjected to the same conditions assessed by Coomassie Blue staining. Molecular weight markers on the left; the position of protein of interest is designated by an arrow to the right.

FIG. 7. SPP cultures can be highly condensed

ACA-less EnvZB was expressed from pColdI(SP-4) along with MazF from pACYCmazF. Cultures were grown to an $OD_{600}$ of 0.5, shifted to 15° C. for 45 min, concentrated to the levels shown and then induced with IPTG for 0 or 21 hr in M9 medium. Samples were subjected to SDS-PAGE followed by Coomassie Blue staining. Molecular weight markers on the left; the position of EnvZB is designated by an arrow to the right.

Figure 8A:
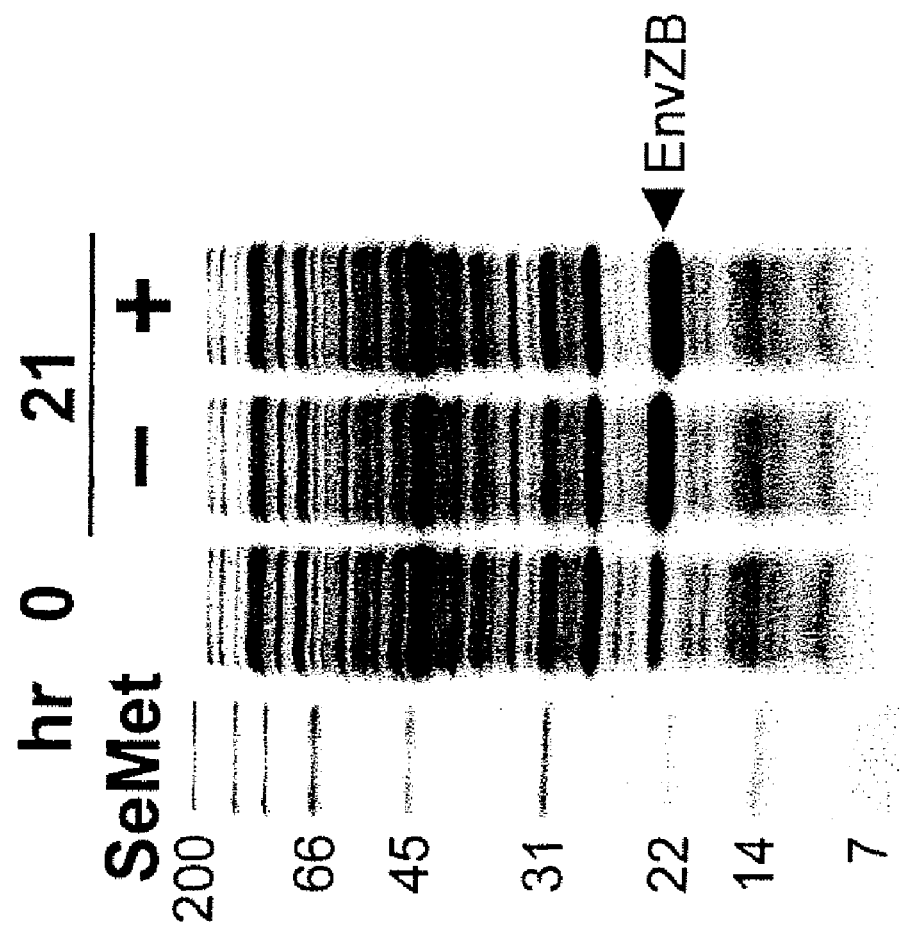
Figure 8B:
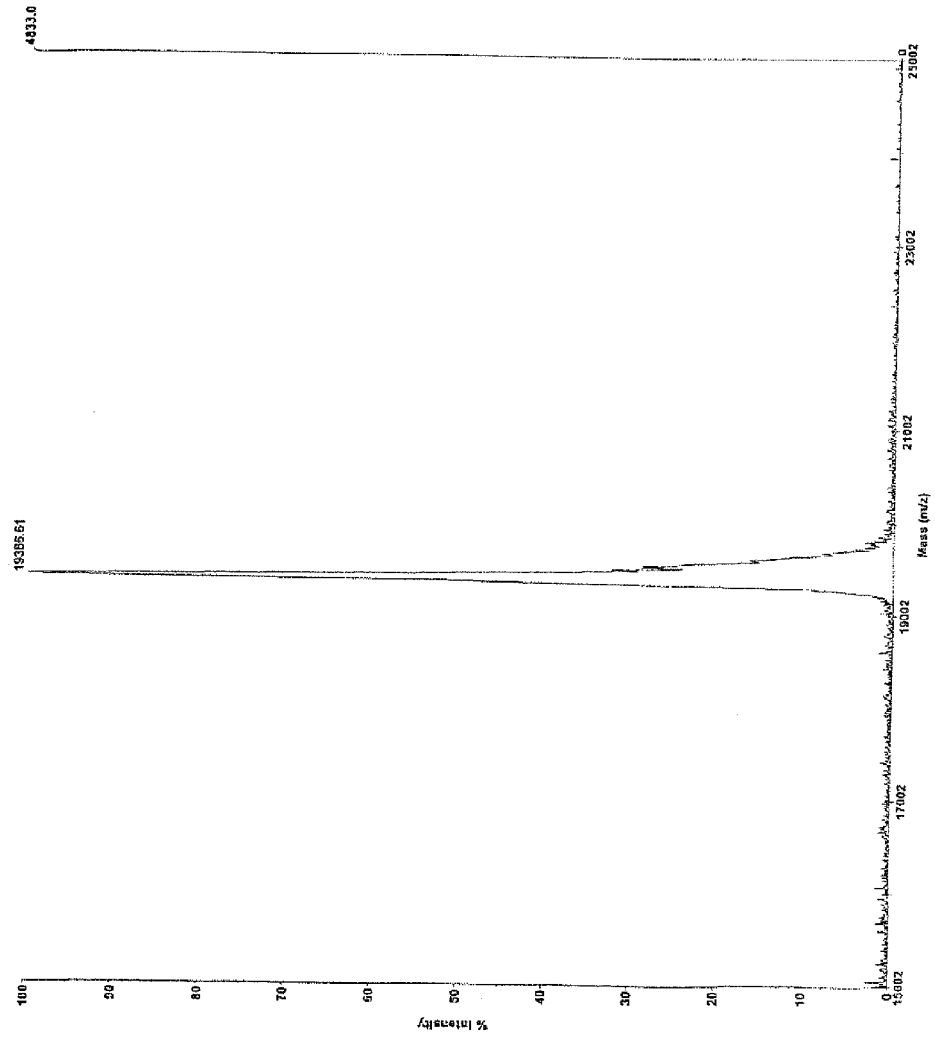
Figure 8C:
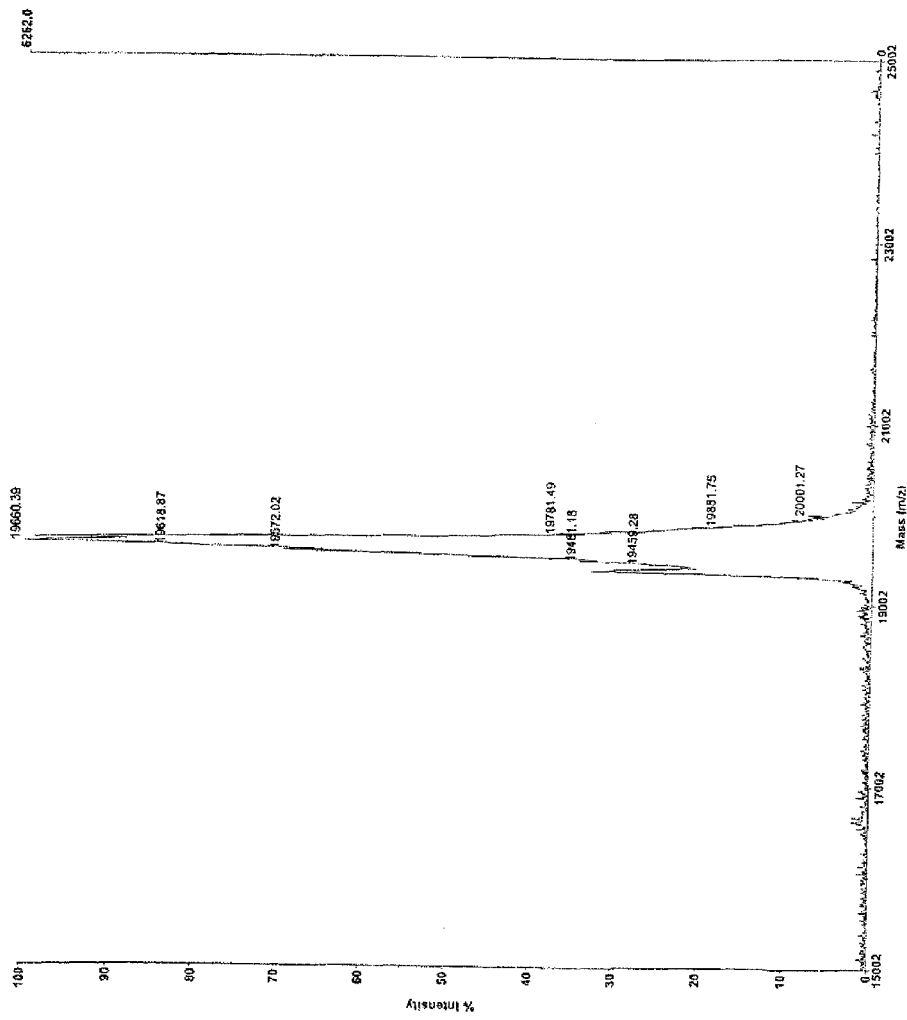

FIG. 8. cSPP facilitates high efficiency selenomethionine substitution without toxicity (A) Bacterial cultures expressing ACA-less EnvZB from pColdI(SP-4) and MazF from pACYCmazF were grown to an $OD_{600}$ of 0.5, shifted to 15° C. for 45 min, concentrated 40 fold and then induced with IPTG for 0 (left lane) or 21 hr in M9 medium with (right lane) or without (middle lane) selenomethionine. Samples were subjected to SDS-PAGE followed by Coomassie Blue staining. Molecular weight markers on the left; the position of EnvZB is designated by an arrow to the right. (B, C) EnvZB expressed with (C) or without (B) selenomethionine was affinity purified through Ni—NTA column and their molecular masses were analyzed by mass spectroscopy.

Figure 9A:
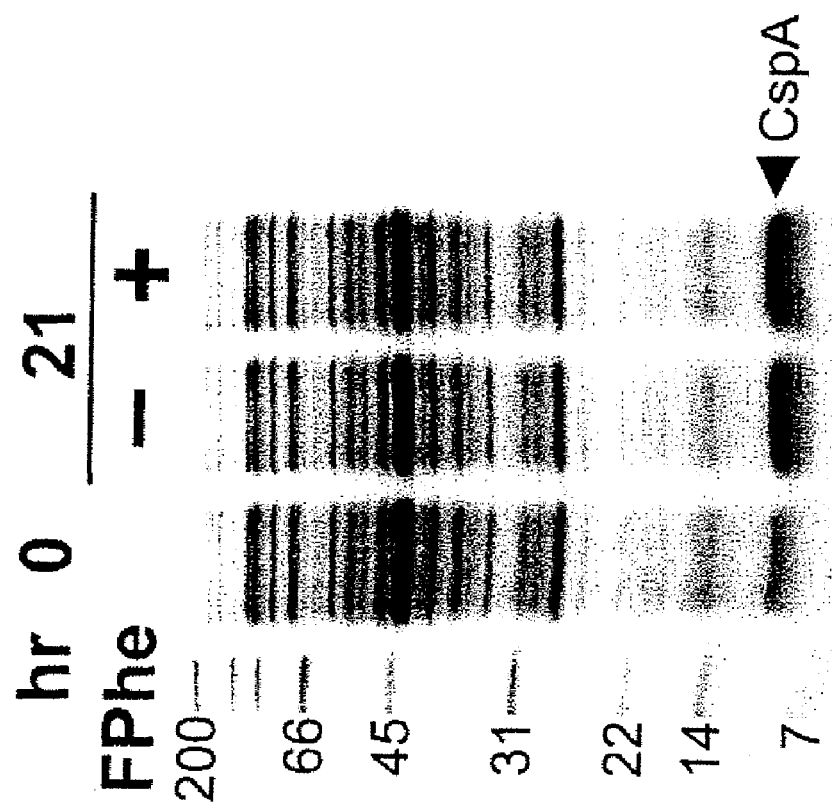
Figure 9B:
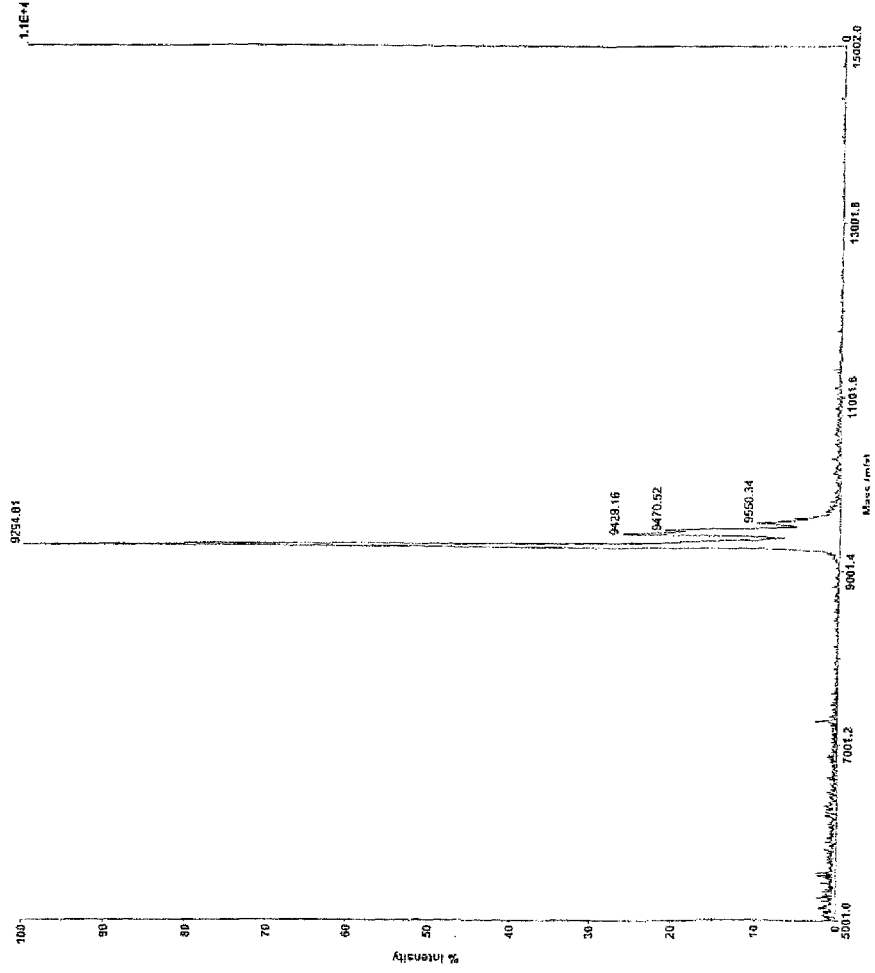
Figure 9C:
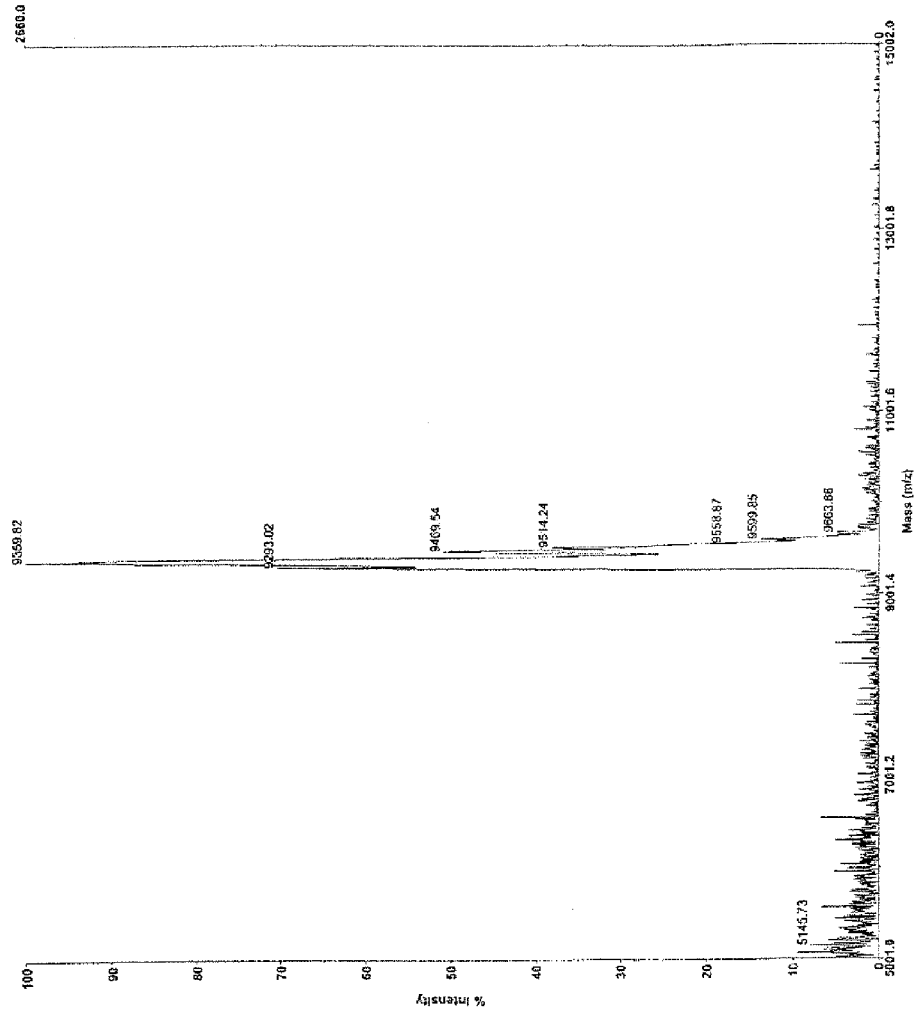

FIG. 9. cSPP enables efficient fluorophenylalanine substitution without toxicity (A) Bacterial cultures expressing ACA-less CspA from pColdI(SP-4) and MazF from pACYCmazF were grown to an $OD_{600}$ of 0.5, shifted to 15° C. for 45 min, concentrated 40 fold and then induced with IPTG for 0 (left lane) or 21 hr in M9 medium with (right lane) or without (middle lane) F-Phe. Samples were subjected to SDS-PAGE followed by Coomassie Blue staining. Molecular weight markers on the left; the position of CspA is designated by an arrow to the right. (B, C) CspA expressed with (C) or without (B) F-Phe was affinity purified and their molecular masses were analyzed by mass spectroscopy.

Figure 10A:
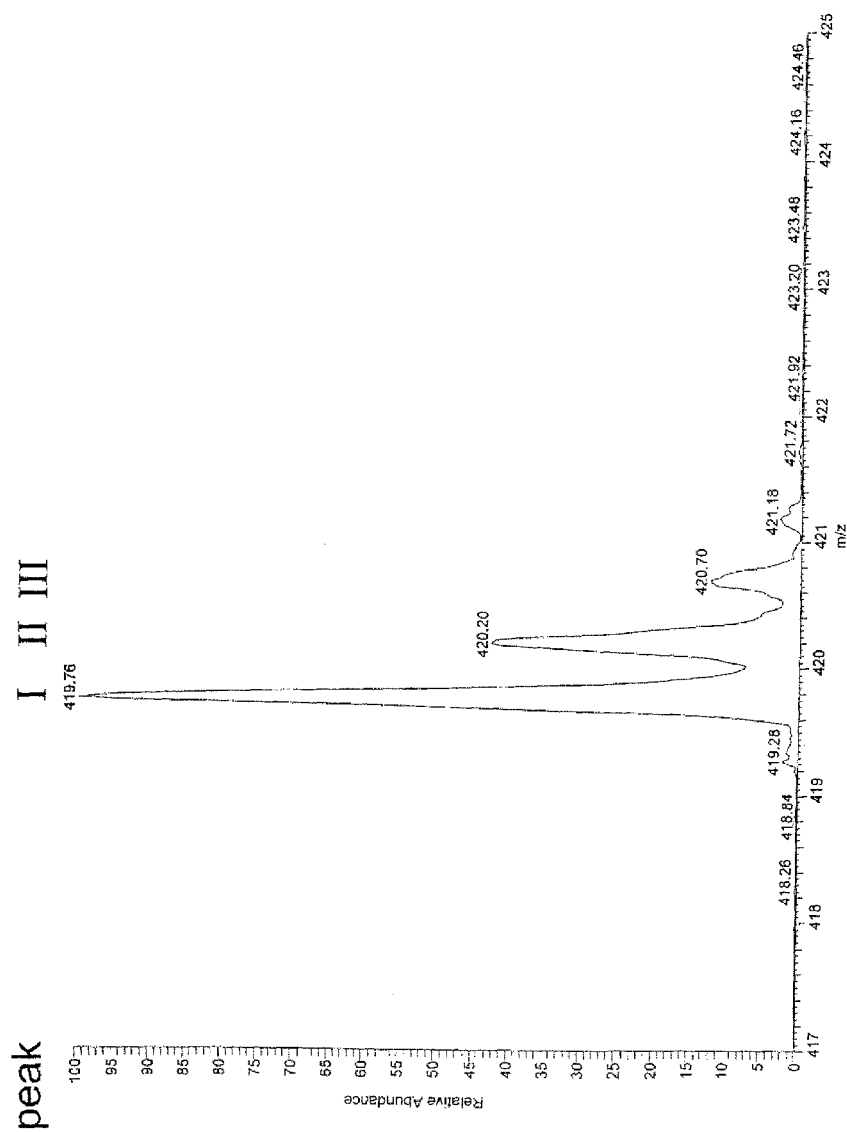
Figure 10B:
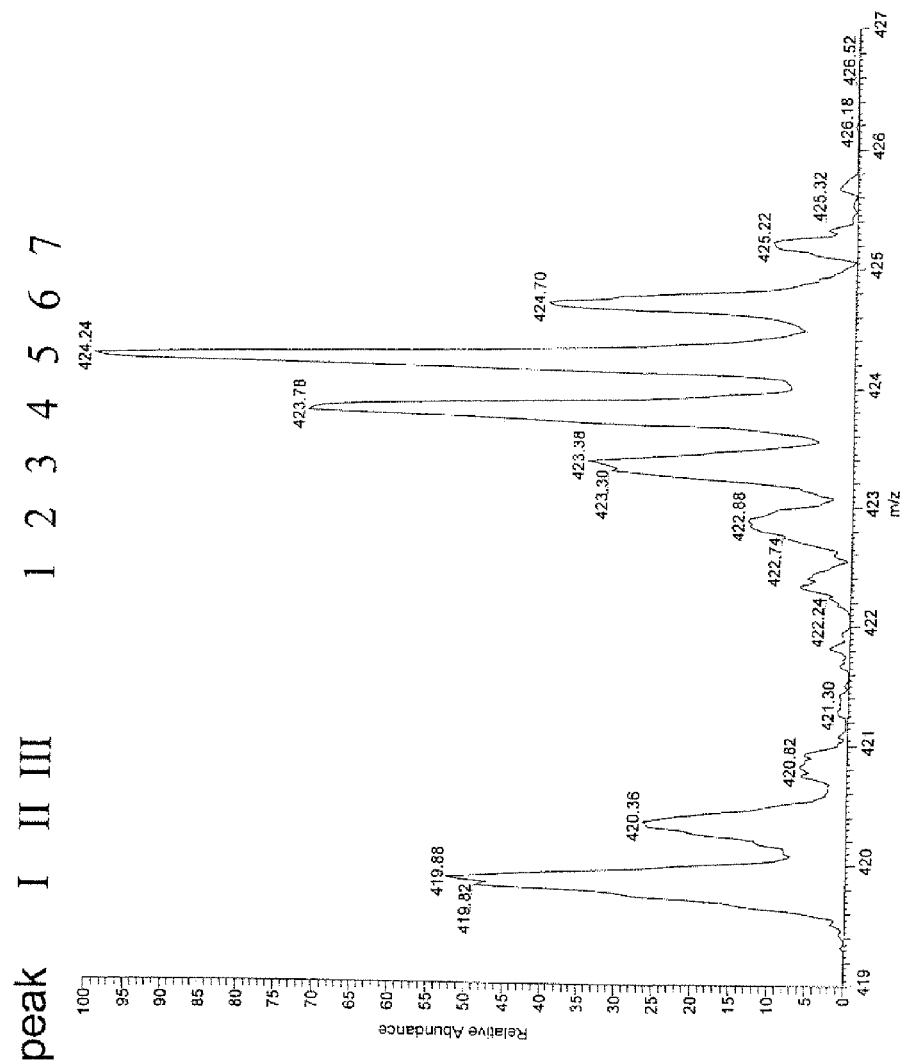

FIG. 10. cSPP cultures incorporate $^{15}$N with very high efficiency

Both panels represent mass spectroscopy of a seven residue YGNGWIK tryptic fragment derived from 20-fold concentrated cultures of ACA-less EnvZB expressed from pColdI (SP-2) along with MazF from pACYCmazF grown in either M9 medium (A) or $^{15}$N-M9 medium (B).

SUMMARY OF THE INVENTION

The present invention describes a single-protein production (SPP) system in living *E. coli* cells that exploits the unique properties of an mRNA interferase, for example, MazF, a bacterial toxin that is a single stranded RNA- and ACA-specific endoribonuclease, which efficiently and selectively degrades all cellular mRNAs in vivo, resulting in a precipitous drop in total protein synthesis. In one embodiment of the present invention, a system for expressing a single target protein in a transformable living cell while reducing non-target cellular protein synthesis includes: (a) an isolated transformable living cell comprising cellular mRNA having at least one first mRNA interferase recognition sequence; (b) a first expression vector comprising an isolated nucleic acid sequence encoding an mRNA interferase polypeptide, wherein the isolated nucleic acid sequence encoding the mRNA interferase polypeptide is mutated by replacing at least one second mRNA interferase recognition sequence with an alternate triplet codon sequence to produce a mutated nucleic acid sequence encoding a mutated mRNA interferase polypeptide; and (c) optionally, a second expression vector comprising an isolated nucleic acid sequence encoding a target protein, wherein the isolated nucleic acid sequence encoding the target protein is mutated by replacing at least one third mRNA interferase recognition sequence with an alternate triplet codon sequence to produce a mutated nucleic acid sequence encoding a mutated target protein; wherein the isolated cell is transformed with the first expression vector and the second expression vector; and wherein the isolated cell is maintained under conditions permitting expression of the mutant target protein in the cell.

In another embodiment, the present invention provides a method of increasing expression of a target protein in an isolated living cell including the steps: (a) mutating an isolated nucleic acid sequence encoding an mRNA interferase polypeptide to replace at least one first mRNA interferase recognition sequence with an alternate triplet codon sequence to produce a mutated nucleic acid sequence encoding a mutated mRNA interferase polypeptide, (b) mutating an isolated nucleic acid sequence encoding the target protein to replace at least one second mRNA interferase recognition sequence with an alternate triplet codon sequence to produce a mutated nucleic acid sequence encoding a mutated target protein; (c) providing a first expression vector comprising the mutated nucleic acid sequence of step (a) and a second expression vector comprising the mutated nucleic acid sequence of step (b); (d) providing an isolated living transformable cell having cellular messenger RNA sequences comprising at least one of a third mRNA interferase recognition sequence, (e) introducing the first expression vector and the second expression vector into the isolated living transformable cell; (f) expressing the mutated mRNA interferase polypeptide, and (g) maintaining the isolated cell under conditions permitting expression of the mutant target protein in the cell.

The present invention also provides an optimized condensed single protein production system.

DETAILED DESCRIPTION OF THE INVENTION

Single Protein Production (SPP) technology in *Escherichia coli* cells[1] exploits the unique properties of MazF, a ssRNA- and ACA-specific endoribonuclease[2] MazF is a bacterial toxin that selectively degrades all cellular mRNAs in vivo, resulting in a precipitous drop in total protein synthesis leading to cell growth arrest. However, when a gene encoding a target protein is engineered to transcribe an ACA-less mRNA, its transcript is stably co-expressed and translated in MazF-induced cells. Codon degeneracy enables alteration of an ACA triplet to a cleavage-resistant sequence without changing the protein amino acid sequence, regardless of its position in the reading frame.

MazF growth arrested cells are "quasi-dormant" since they can be coaxed out of metabolic quiescence by exposure to an appropriate trigger (in this case through exposure to an ACA-less mRNA). Remarkably, the host cell translation machinery remains functional, enabling the expression of recombinant proteins at high levels without significant background cellular protein synthesis. In fact, in spite of being growth arrested, MazF-induced cells retain the full spectrum of biosynthetic functions necessary to support mRNA transcription and translation[1].

Here we optimize the SPP system expression plasmids, determine that MazF-induced quasi-dormant cells can sustain single protein production for up to one week, show that culture condensation can be implemented to impart dramatic cost savings without sacrificing protein yield and that high level incorporation of amino acid analogs into target proteins is not cytotoxic to SPP cells. The applications for this improved expression system are multifold and of particular utility for large scale structural genomics projects that employ both NMR and X-ray crystallography.

We have demonstrated that the cSPP system represents a significant improvement in our original SPP system. There are five major attributes of this new system. First, we modified the expression vector and showed that it supported the best overall SPP expression of a variety of proteins. Second, we have demonstrated that SPP synthesis can occur for at least seven days, indicating that recycling of the components required for translation (tRNA and ribosomes) undoubtedly occurs. Therefore, there appears to be no theoretical limit to the size of the protein that can be synthesized by the SPP system. Third, with the goal of reducing the cost of the amino acid substitution and isotope labeling steps for X-ray crystallography and NMR structure applications, we first demonstrated that a 40-fold culture condensation step (to >$10^{10}$ cells/ml) does not significantly reduce protein yields (the expressed protein comprises 20-30% of total cellular proteins or the yield of as high as 1-1.5 mg/ml for target protein). Forth, the cost efficiencies afforded by the cSPP system result in a dramatic decrease—to only 2.5% the expense of typical incorporation experiments—in the cost of medium containing relatively expensive amino acid analogs or isotopes. Finally, we demonstrated that these cSPP conditions support high levels of $^{15}N$ incorporation as well as very efficient incorporation of toxic amino acids such as selenomethionine and F-Phe substitution without the characteristic cytotoxicity that can preclude protein structure determination. The 90% incorporation of selenomethionine is close to that achieved in vitro incorporation systems[7] and is well within level required for excellent MAD phasing.

The ability of the cSPP cells to tolerate culture condensation and avoid amino acid analog cytotoxicity stems from the unique physiological state of the *E. coli* cells during cSPP inducing conditions. MazF induced quasi-dormant cells are not actively growing—the optical density of cultures does not increase—hence, their nutritional demands are not as high as actively growing cells. Also, since MazF acts to selectively degrade virtually all mRNAs in vivo, almost no background protein synthesis occurs. Therefore, selenomethionine or other cytotoxic amino acid analogs are not generally incorporated into cellular proteins. This enables the production of pure target protein with high levels of selenomethionine or other amino acid analogs without the secondary cytotoxic effects.

Although cSPP and SPP systems call for the construction of an ACA-less target gene (thus encoding an ACA-less mRNA), there are two approaches to quickly and economically address this requirement. If the target gene contains only a few ACA sequences, these sequences can be altered by oligonucleotide-directed site-specific mutagenesis so that they are no longer cleavable by MazF. However, if a gene is large and/or has many ACA sequences, the best approach is to chemically synthesize the entire gene using one of the commercially available gene synthesis technologies (e.g. Codon Devices, Cambridge, Mass.[10]) This general approach has several advantages. First, the gene sequences are guaranteed for accuracy so the subsequent sequence verification step that typically follows PCR mutagenesis is no longer necessary. Second, the synthetic gene can be directly inserted into a vector of choice, eliminating the need for a cloning step. Third, in an effort to improve translation efficiency, the gene sequence can be optimized to the codon usage preferences of the particular organism used for expression. Finally, the time and manpower savings more than offset the modest cost of whole gene synthesis. As with new technologies in general, the cost should continue to fall as the methods used for gene synthesis become further improved. In fact, we expect that this technology will completely replace PCR mediated site-directed mutagenesis for creation of ACA-less genes in the next few years.

As with our original SPP system, protein production using cSPP generates high signal-to-noise ratios without any purification steps because essentially only the target protein is labeled with isotopes/analogs because background cellular protein synthesis is virtually absent. Therefore, NMR structural studies of the protein may be carried out without purification. This attribute is especially attractive for membrane proteins. Furthermore, the high signal-to-noise ratio enables us to explore the potential for stabilizing the folded state of a protein by compartmentalization inside the living cell using In-Cell NMR spectroscopy[11-13]. In-Cell NMR is the only way to learn about the actual structures and dynamics of proteins inside of living cells under truly physiological conditions.

The following definitions set forth the parameters of the present invention.

The abbreviation "ACA" refers to the sequence Adenine-Cytosine-Adenine. As used herein, the terms "encode", "encoding" or "encoded", with respect to a specified nucleic acid, refers to information stored in a nucleic acid for translation into a specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

The term "codon" as used herein refers to triplets of nucleotides that together specify an amino acid residue in a polypeptide chain. Most organisms use 20 or 21 amino acids to make their polypeptides, which are proteins or protein precursors. Because there are four possible nucleotides, adenine (A), guanine (G), cytosine (C) and thymine (T) in DNA, there are 64 possible triplets to recognize only 20 amino acids plus the termination signal. Due to this redundancy, most amino acids are coded by more than one triplet. The codons that specify a single amino acid are not used with equal frequency. Different organisms often show particular "preferences" for one of the several codons that encode the same given amino acids. If the coding region contains a high level or a cluster of rare codons, removal of the rare codons by resynthesis of the gene or by mutagenesis can increase expression. See J. Sambrook and D. W. Russell, Molecular Cloning, A Laboratory Manual, Third Edition, Cold Spring Harbor Press, Cold Spring Harbor, N.Y. (2001), at 15.12; which is incorporated herein by reference. "Codon selection" therefore may be made to optimize expression in a selected host. The most preferred codons are those which are frequently found in highly expressed genes. For "codon preferences" in *E. coli*, see Konigsberg, et al., Proc. Nat'l. Acad. Sci. U.S.A. 80:687-91 (1983), which is incorporated herein by reference.

One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons UUA, UUG, CUU, CUC, CUA, and CUG all encode the amino acid leucine. Thus, at every position where a leucine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is within the scope of the present invention.

The term "eotaxin" as used herein refers to a chemotactic factor consisting of 74 amino acid residues that belongs to the C—C (or beta) chemokine family and has been implicated in animal and human eosinophilic inflammatory states.

The present invention includes active portions, fragments, derivatives, mutants, and functional variants of mRNA interferase polypeptides to the extent such active portions, fragments, derivatives, and functional variants retain any of the biological properties of the mRNA interferase. An "active portion" of an mRNA interferase polypeptide means a peptide that is shorter than the full length polypeptide, but which retains measurable biological activity. A "fragment" of an mRNA interferase means a stretch of amino acid residues of at least five to seven contiguous amino acids, often at least about seven to nine contiguous amino acids, typically at least about nine to thirteen contiguous amino acids and, most preferably, at least about twenty to thirty or more contiguous amino acids. A "derivative" of an mRNA interferase or a fragment thereof means a polypeptide modified by varying the amino acid sequence of the protein, e.g., by manipulating the nucleic acid encoding the protein or by altering the protein itself. Such derivatives of the natural amino acid sequence may involve insertion, addition, deletion, or substitution of one or more amino acids, and may or may not alter the essential activity of the original mRNA interferase.

The term "gene" refers to an ordered sequence of nucleotides located in a particular position on a segment of DNA that encodes a specific functional product (i.e, a protein or RNA molecule). It can include regions preceding and following the coding DNA as well as introns between the exons.

The term "induce" or "inducible" refers to a gene or gene product whose transcription or synthesis is increased by exposure of the cells to an inducer or to a condition, e.g., heat.

The terms "inducer" or "inducing agent" refer to a low molecular weight compound or a physical agent that associates with a repressor protein to produce a complex that no longer can bind to the operator.

The term "induction" refers to the act or process of causing some specific effect, for example, the transcription of a specific gene or operon, or the production of a protein by an organism after it is exposed to a specific stimulus.

The terms "introduced", "transfection", "transformation", "transduction" in the context of inserting a nucleic acid into a cell, include reference to the incorporation of a nucleic acid into a prokaryotic cell or eukaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is substantially free from components that normally accompany or interact with it as found in its naturally occurring environment. The isolated material optionally comprises material not found with the material in its natural environment; or, if the material is in its natural environment, the material has been synthetically (non-naturally) altered by deliberate human intervention. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The abbreviation "IPTG" refers to isopropyl-beta-D-thiogalactopyranoside, which is a synthetic inducer of beta-galactosidase, an enzyme that promotes lactose utilization, by binding and inhibiting the lac repressor. For example, IPTG is used in combination with the synthetic chromogenic substrate Xgal to differentiate recombinant from non-recombinant bacterial colonies in cloning strategies using plasmid vectors containing the lacZ gene.

The term "MazF" as used herein refers to the general class of endoribonucleases, to the particular enzyme bearing the particular name, and active fragments and derivatives thereof having structural and sequence homology thereto consistent with the role of MazF polypeptides in the present invention.

The abbreviation "lspA" refers to the gene responsible for signal peptidase II activity in *E. coli*.

The abbreviation "LspA" refers to the gene responsible for Lipoprotein Signal Peptidase activity in *E. coli*.

The family of enzymes encompassed by the present invention is referred to as "mRNA interferases". It is intended that the invention extend to molecules having structural and functional similarity consistent with the role of this family of enzymes in the present invention.

As used herein, the term "nucleic acid" or "nucleic acid molecule" includes any DNA or RNA molecule, either single or double stranded, and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. Unless otherwise limited, the term encompasses known analogues.

The term "oligonucleotide" refers to a nucleic acid molecule comprised of two or more ribo- or deoxyribonucleotides, preferably more than three, joined by phosphodiester bonds.

The term "operator" refers to the region of DNA that is upstream (5') from a gene(s) and to which one or more regulatory proteins (repressor or activator) bind to control the expression of the gene(s)

As used herein, the term "operon" refers to a functionally integrated genetic unit for the control of gene expression. It consists of one or more genes that encode one or more polypeptide(s) and the adjacent site (promoter and operator) that controls their expression by regulating the transcription of the structural genes. The term "expression operon" refers to a nucleic acid segment that may possess transcriptional and translational control sequences, such as promoters, enhancers, translational start signals, polyadenylation signals, terminators, and the like, and which facilitate the expression of a polypeptide coding sequence in a host cell or organism.

The phrase "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The abbreviation "ORF" stands for "open reading frame, a portion of a gene's sequence that contains a sequence of bases, uninterrupted by internal stop sequences, and which has the potential to encode a peptide or protein. Open reading frames start with a start codon, and end with a termination codon. A termination or stop codon determines the end of a polypeptide.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The abbreviation "PCR" refers to polymerase chain reaction, which is a technique for amplifying the quantity of DNA, thus making the DNA easier to isolate, clone and sequence. See, e.g., U.S. Pat. Nos. 5,656,493, 533,675, 5,234,824, and 5,187,083, each of which is incorporated herein by reference.

As used herein the term "promoter" includes reference to a region of DNA upstream (5') from the start of transcription and involved in recognition and binding of RNA polymerase and other proteins to initiate transcription. The term "inducible promoter" refers to the activation of a promoter in response to either the presence of a particular compound, i.e., the inducer or inducing agent, or to a defined external condition, e.g., elevated temperature.

The phrase "site-directed mutagenesis" refers to an in vitro technique whereby base changes i.e., mutations, are introduced into a piece of DNA at a specific site, using recombinant DNA methods.

The term "untranslated region" or UTR, as used herein refers to a portion of DNA whose bases are not involved in protein synthesis.

The terms "variants", "mutants" and "derivatives" of particular sequences of nucleic acids refer to nucleic acid sequences that are closely related to a particular sequence but which may possess, either naturally or by design, changes in sequence or structure. By "closely related", it is meant that at least about 60%, but often, more than 85%, of the nucleotides of the sequence match over the defined length of the nucleic acid sequence. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce protein variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan.

As used herein, the terms "vector" and "expression vector" refer to a replicon, i.e., any agent that acts as a carrier or transporter, such as a phage, plasmid, cosmid, bacmid, phage or virus, to which another genetic sequence or element (either DNA or RNA) may be attached so as to bring about the replication of the attached sequence or element and so that sequence or element can be conveyed into a host cell. The *E. coli* SPP system described herein utilizes pColdI vectors, which induce protein production at low temperatures.

It must be noted that as used herein and in the appended claims, the singular forms "a", "and", and "the" include plural referents unless the context clearly dictates otherwise. All technical and scientific terms used herein have the same meaning.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Strains and Plasmids

E. coli BL21(DE3) cells were used in the experiments described below. The mazF gene was cloned into the NdeI-XhoI sites of pACYCDuet (Novagen) to create plasmid pACYCmazF. pACYCmazF(−9ACA) was constructed by site-directed mutagenesis using pACYCmazF as template. The eotaxin gene was synthesized on the basis of the optimal E. coli codon usage (See FIG. 2A; SEQ ID NO:1) and cloned into the NdeI-HindIII sites of pColdI(SP-1) to create plasmid pColdI(SP-1)eotaxin. pColdI(SP-1)eotaxin was constructed as described in the text by site-directed mutagenesis using pColdI(eotaxin) as template. Mutagenesis was carried out using Pfu DNA polymerase (Stratagene) according to the instructions for the QuickChange Site-Directed Mutagenesis Kit (Stratagene). pColdI(SP-2)eotaxin was also constructed by site-directed mutagenesis using pColdI(SP-1)eotaxin as template. pColdI(SP-1)eotaxin(+ACA) was constructed by site-directed mutagenesis using pColdI(SP-1)eotaxin as template. The wildtype Hsp10 gene was amplified by PCR with Yeast chromosome as template and cloned into the NdeI-BamHI sites of pColdI(SP-2) to create plasmid pColdI(SP-2)Hsp10. The ACA-less Hsp10 gene was amplified by two-step PCR with Yeast chromosome as template and cloned into the NdeI-BamHI sites of pColdI(SP-2) to create plasmid pColdI(SP-2)Hsp10(−ACA). The wild-type and ACA-less Rpb12 gene was amplified by PCR with wild type Rpb12 plasmid as template and 5' and 3' oligonucleotides containing the altered sequence cloned into the NdeI-BamHI sites of pColdI(SP-2) to create plasmid pColdI(SP-2)Rpb12 and pColdI(SP-2)Rpb12(−ACA), respectively. The ACA-less LspA gene was amplified by two-step PCR and cloned into the NdeI-BamHI sites of pColdIV(SP-2) to create plasmid pColdIV(SP-2)lspA(−ACA).

Assays of Protein Synthesis in Vivo

E. coli BL21(DE3) carrying plasmids was grown in M9-glucose medium. When the $OD_{600}$ of the culture reached 0.5, the culture was shifted to 15° C. for 45 min and 1 mM of IPTG was added to the culture. At the indicated time intervals, 1 ml of culture was added to a test tube containing 10 mCi [$^{35}$S]-methionine. After incubation for 15 min (pulse), 0.2 ml of 40 mg/ml methionine was added and incubated for another 5 min (chase). The labeled cells were washed with M9-glucose medium and suspended in 100 μl of SDS-PAGE loading buffer. 10 μl of each sample was analyzed by SDS-PAGE followed by autoradiography.

Preparation of the Membrane Fraction

The cells harvested from 1 ml of culture by centrifugation (10,000×g for 5 min) were suspended in the 10 mM Tris-HCl (pH 7.5) and disrupted by sonication. The total membrane fraction was obtained by centrifugation (100,000×g, for 60 min) after the removal of unbroken cells.

Example 1

Effects of MazF Induction of Cellular Protein Synthesis

E. coli BL21(DE3) carrying pACYCmazF was transformed either with pColdI(SP-1)eotaxin (A and left panel in B) or pColdI(SP-2)eotaxin (right panel in B and C). Cells were grown in M9 medium at 37° C. At $OD_{600}$ of 0.5, the cultures were shifted to 15° C. and after incubation at 15° C. for 45 min to make cells acclimate low temperature, IPTG (1 mM) was added to induce both eotaxin and MazF expression (0 time). Cells were pulse-labeled with $^{35}$S-methionine for 15 min at the time points indicated on top of each gel and total cellular proteins were analyzed by SDS-polyacryalminde gel electrophoresis (PAGE) followed by autoradiography.

The mazF gene was cloned into pACYC, a low copy number plasmid containing an IPTG inducible phage T7 promoter, yielding pACYCmazF. Cloning techniques generally may be found in J. Sambrook and D. W. Russell, Molecular Cloning: A Laboratory Manual, Third Edition, Cold Spring Harbor Press, Cold Spring Harbor, N.Y. (2001), which is incorporated herein by reference. E. coli BL21 (DE3) transformed with pACYCmazF was sensitive to IPTG, a lac inducer, as no colonies were formed on agar plates containing IPTG (not shown).

Figure 1A:
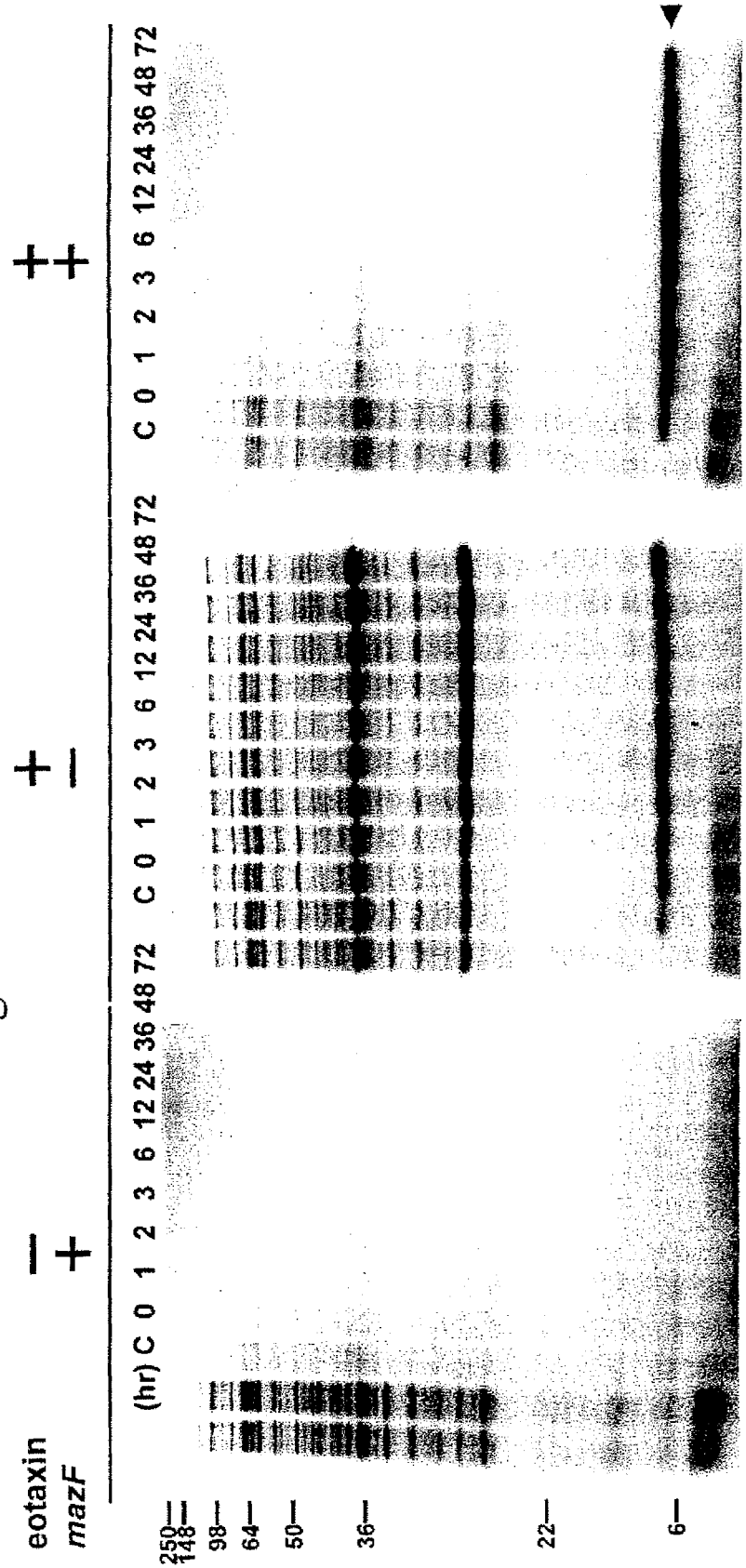
FIG. 1. Expression of Human Eotaxin with Use of pColdI (SP-1) and pColdI(SP-2) with and without MazF Coexpression FIG. 2. Effect of ACA Sequences on Eotaxin Expression FIG. 3. Effect of Removal of All ACA Sequences in the MazF ORF on Eotaxin Expression FIG. 4. Expression of Yeast Proteins in the SPP System FIG. 5. Expression of LspA, an Inner Membrane Protein in the SPP System Using pColdIV(SP-2).
Figure 1B:
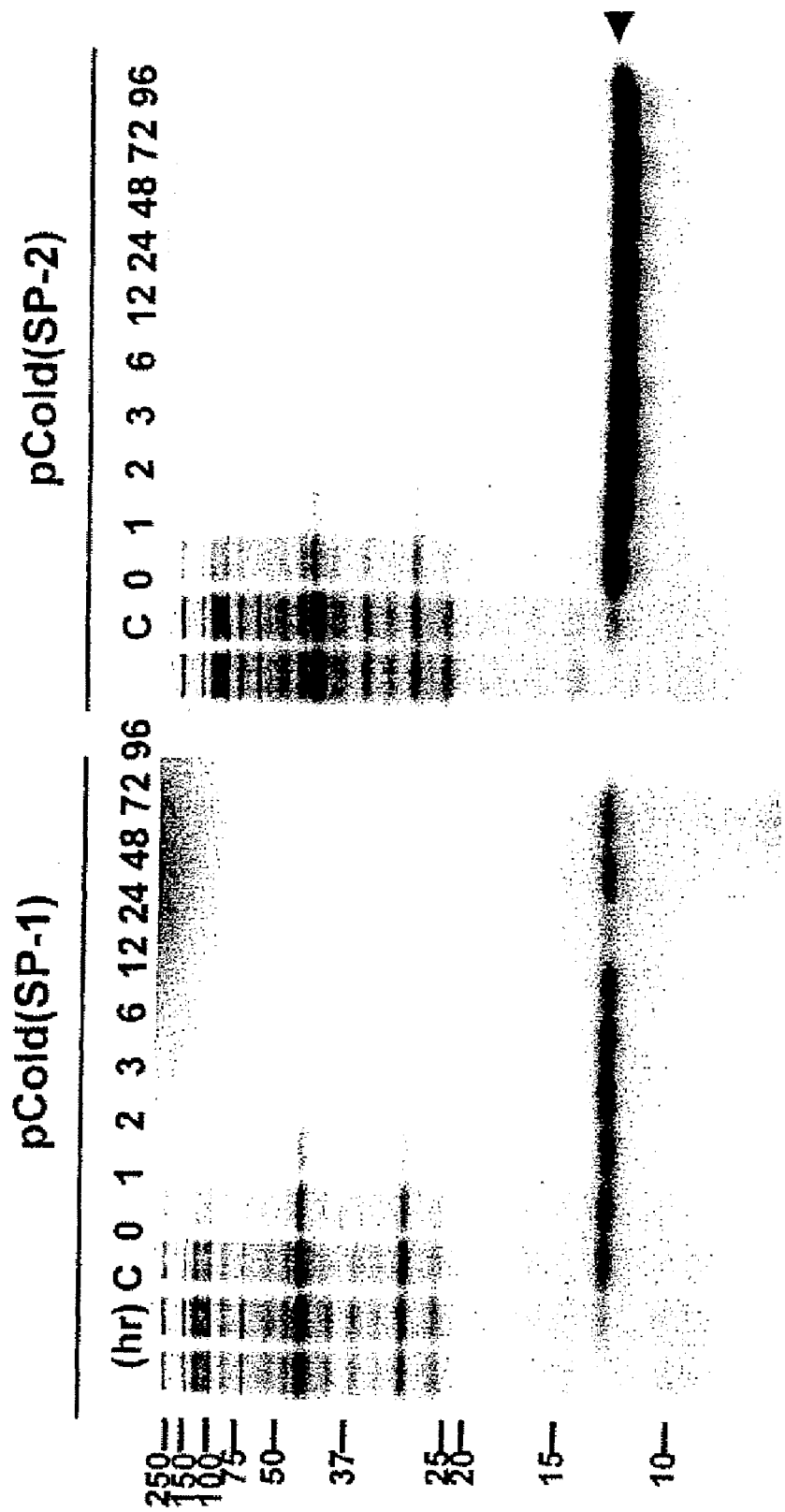

FIG. 1 shows the expression of Human Eotaxin with Use of pColdI(SP-1) and pColdI(SP-2) with and without MazF coexpression by SDS-PAGE. FIG. 1B shows the results for cells transformed with pColdI(SP-1)eotaxin (left panel); and transformed with pColdI(SP-2)eotaxin (right panel). FIG. 1C shows the results for cells transformed with pACYCmazF and pColdI(SP-2)eotaxin were incubated in LB (left panel) or M9 medium (right panel). Cells were treated in the same manner as in FIG. 1A and FIG. 1B, and, at the time points indicated, total cellular proteins were analyzed by SDS-PAGE followed by Coomassie Blue staining. Note that the same volumes of the cultures were taken for the analysis. Positions of molecular weight markers are shown at the left hand side of the gels and the position of eotaxin is indicated by an arrow. As MazF effectively cleaves mRNAs at ACA sequences, cellular protein synthesis was dramatically inhibited at 37° C. upon MazF induction (Zhang et al., Mol. Cell 12: 913-23 (2003)) or at 15° C. as shown in FIG. 1A. In this cold-shock experiment, cells carrying pACYCmazF were first incubated for 45 min at 15° C. to induce cold-shock proteins required for cold-shock acclimation (see Thieringer et al., Bioassays 20(1): 49-57 (1998)). Then IPTG was added to the culture to induce MazF (0 time in FIG. 1A, left panel). Cells were pulse-labeled with [$^{35}$S] methionine for 15 min at the time points indicated on top of the gel. Panel A left panel shows the results for cells transformed only with pACYCeotaxin; panel A middle panel shows the results for cells transformed only with pCold(SP-1)eotaxin; and Panel A right panel shows the results for cells transformed with both plasmids.

At 0 time, a very similar protein pattern was observed as that of the cells in the absence of IPTG (control, indicated as C), while cellular protein synthesis was dramatically inhibited at 1 hr after the addition of IPTG. After 6 hr, the synthesis of almost all cellular proteins was almost completely blocked.

Example 2

Expression of an ACA-Less mRNA in MazF-Induced Cells

We speculated that if an mRNA that is engineered to contain no ACA sequences is expressed in MazF-induced cells, the mRNA might be stably maintained in the cells so that the protein encoded by the mRNA may be produced without producing any other cellular proteins. To test this possibility, we synthesized the gene for human eotaxin, eliminating all ACA sequences in the gene without altering the amino acid sequence. FIG. 2A shows the amino acid sequence of human eotaxin and the nucleotide sequences of its gene. The nucleotide sequence was designed using preferred E. coli codons and those triplets underlined were changed to ACA in the experiment below. The ACA sequence is unique among 64 possible triplet sequences, as it can be altered to other MazF-uncleavable sequences without changing the amino acid sequence of a protein regardless of the position of an ACA sequence in a reading frame.

The eotaxin gene shown in FIG. 2A (SEQ ID NO:1) was fused with a 17-residue sequence consisting of a sequence from a translation enhancing element from the cspA gene for the major cold-shock protein, CspA (Qing et al Nat. Biotechnol. 22: 877-882 (2004)), 6 His residues, factor Xa cleavage site and the His-Met sequence derived from the NdeI site for gene insertion. The entire coding region for the fusion protein was inserted into pColdI(SP-1) and pColdI(SP-2) vectors, cold-shock vectors allowing a high protein expression upon cold shock (Qing et al, Nat. Biotechnol. 22: 877-882 (2004)). In pCold(SP-1) two ACA sequences, one between the Shine-Dalgarno sequence and the initiation codon and the other in the translation enhancing element were converted to AUA. In pColdI(SP-2) in addition to the two ACA sequences in pColdI (SP-1) three other ACA sequences in the 5'-untranslated region (5'-UTR) also were altered to MazF-uncleavable sequences by base substitutions (to GCA, AUA and GCA from the 5' ACA to the 3, ACA, respectively). The resulting constructs, pColdI(SP-1) eotaxin and pColdI(SP-2)eotaxin, respectively, were transformed into E. coli BL21 (DE3) cells.

After the cells transformed with pColdI(SP-1)eotaxin were cold-shocked at 15° C. and acclimated to the low temperature for 1 hr, IPTG was added to induce eotaxin production. Cells then were pulse-labeled with [$^{35}$S]methionine for 15 mm (0 time; FIG. 1A, middle panel). Eotaxin was produced almost at a constant level from 0 time during 72 hr incubation together with other cellular proteins. The production of eotaxin at the 12 hr time point was approximately 11% of total cellular protein synthesis as judged from [$^{35}$S]methionine incorporation.

When both eotaxin and mazF genes were coexpressed using E. coli BL21 (DE3) harboring both pACYCmazF and pColdI(SP-1)eotaxin, background cellular protein synthesis was dramatically reduced after 3 hr induction, while eotaxin production continued for 72 hr at an almost constant level (FIG. 1A, right panel). Interestingly the level of eotaxin production in this experiment was higher (FIG. 1A, right panel; 11% of total protein production at 12 hr) than that in the absence of MazF induction (FIG. 1A, middle panel; 47% at 12 hr). This approximately 5 fold enrichment is likely due to the fact that more ribosomes became available for eotaxin mRNA translation as cellular mRNAs were degraded by MazF. Notably, no specific protein bands were observed after the 12 hr time point.

When the identical experiment was carried out with the cells harboring both pACYCmazF and pColdI(SP-2)eotaxin, eotaxin was almost exclusively produced (FIG. 1B, right panel). Notably, eotaxin production was substantially higher than that with pColdI(SP-1)eotaxin (FIG. 1B, left panel). This higher production of eotaxin is likely due to the stabilization of the eotaxin mRNA by further removal of ACA sequences in the 5'-UTR in pColdI(SP-1). Approximately 90% of [$^{35}$S] methionine was incorporated into eotaxin at 12 hr after MazF induction and notably no distinct cellular protein bands were discernible (FIG. 1B, right panel) indicating that the signal-to-noise ratio of eotaxin was dramatically improved by the present SPP system. It is interesting to note that the high level of eotaxin production did not diminish even 96 hr after induction. Furthermore, background cellular protein synthesis diminished sooner (at 3 hr) than that with pColdI(SP-1)eotaxin (at 6 hr) (compare the left panel with the right panel in FIG. 1B).

With both vectors (FIGS. 1A and B), cell growth was completely blocked upon MazF induction as judged by $OD_{600}$ and also by [$^{35}$S]methionine incorporation into cellular proteins. These results indicate that growth-arrested cells by MazF induction are not physiologically dead and instead are fully capable of synthesizing proteins if their mRNAs have no ACA sequences. This in turn indicates that the cellular integrity of the E. Coli BL21 (DE3) cells is kept intact for a long period of time so that not only energy metabolism but also biosynthetic functions for amino acids and nucleotides are fully active in the growth-arrested cells. Furthermore, transcriptional and translational machineries are also well maintained including RNA polymerase, ribosomes, tRNA, and all the other factors required for protein synthesis.

The production of eotaxin with pColdI(SP-2) eotaxin appears as a major band by Coomassie Blue staining after SDS polyacrylamide gel electrophoresis (FIG. 1 C). At the 0 hr time point, the eotaxin band was barely discernable while at 12 hr it became the major band and its density increased even more after 24 hr. However, longer incubation did not significantly enhance the level of its production, suggesting that there is a threshold level of eotaxin production in MazF-induced cells. Since the [$^{35}$S]methionine incorporation was constantly maintained for 96 hr (FIG. 1B), its seems that eotaxin production and degradation in the SPP system may equilibrate after 24 hr. It is important to note that the density of the bands for cellular proteins remained constant as expected from complete growth inhibition upon MazF induction. We examined if eotaxin production is affected by rich media such as LB medium and found that the use of LB medium did not enhance eotaxin production any more than the level obtained with defined M9 medium if pColdI(SP-2) was used.

Example 3

The Negative Effect of ACA Sequences on Protein Production

In order to confirm that the exclusive eotaxin production in MazF-induced cells observed in FIG. 1 is due to the ACA-less mRNA for eotaxin, the five native ACA sequences were added to the eotaxin gene without altering its amino acid sequence as shown in FIG. 2A (SEQ ID NO: 1 and SEQ ID NO: 3). The eotaxin genes were expressed with use of pColdI (SP-2) and cells were treated and labeled with [$^{35}$S]-methionine in the same manner as described in FIG. 1. The left panel shows the results for the ACA-less eotaxin gene (same as the left panel of FIG. 1B) and the right panel shows the results for the eotaxin gene with 5 ACA sequences.

Figure 2B:
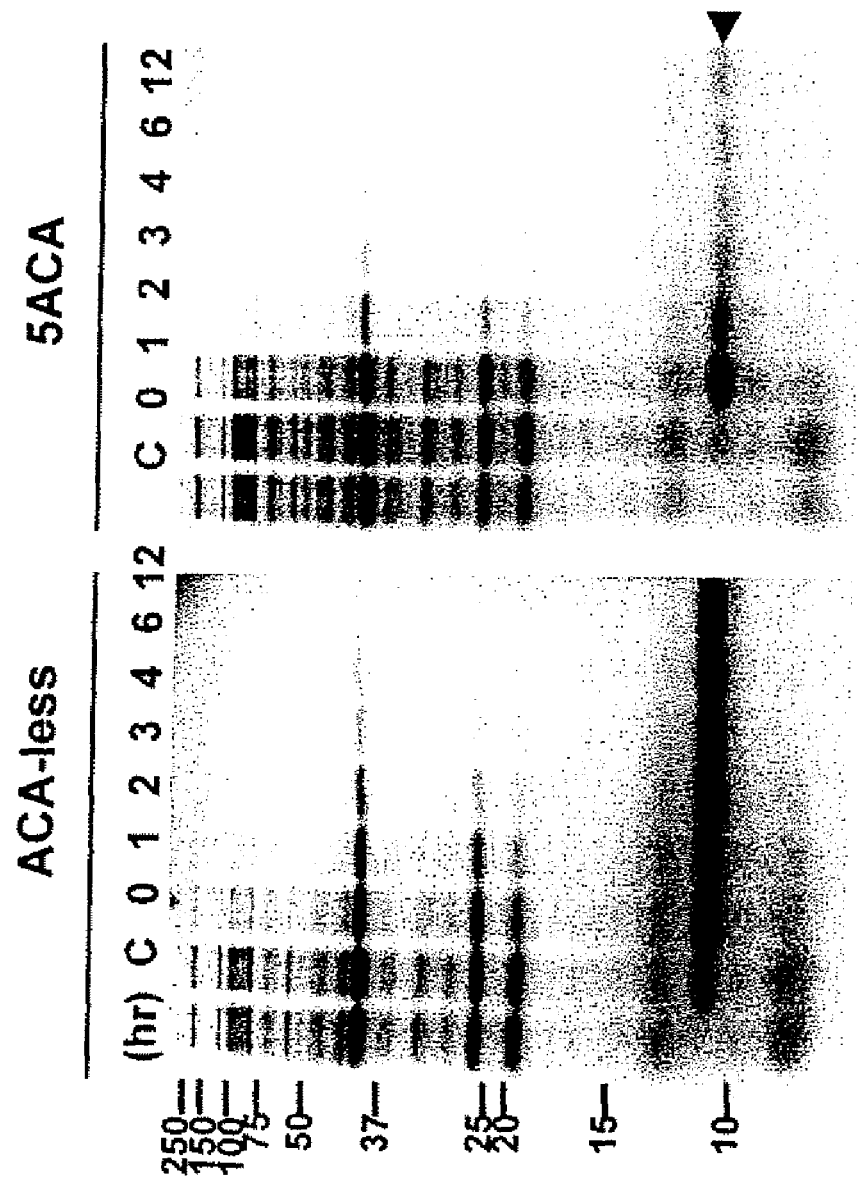
Figure 6A:
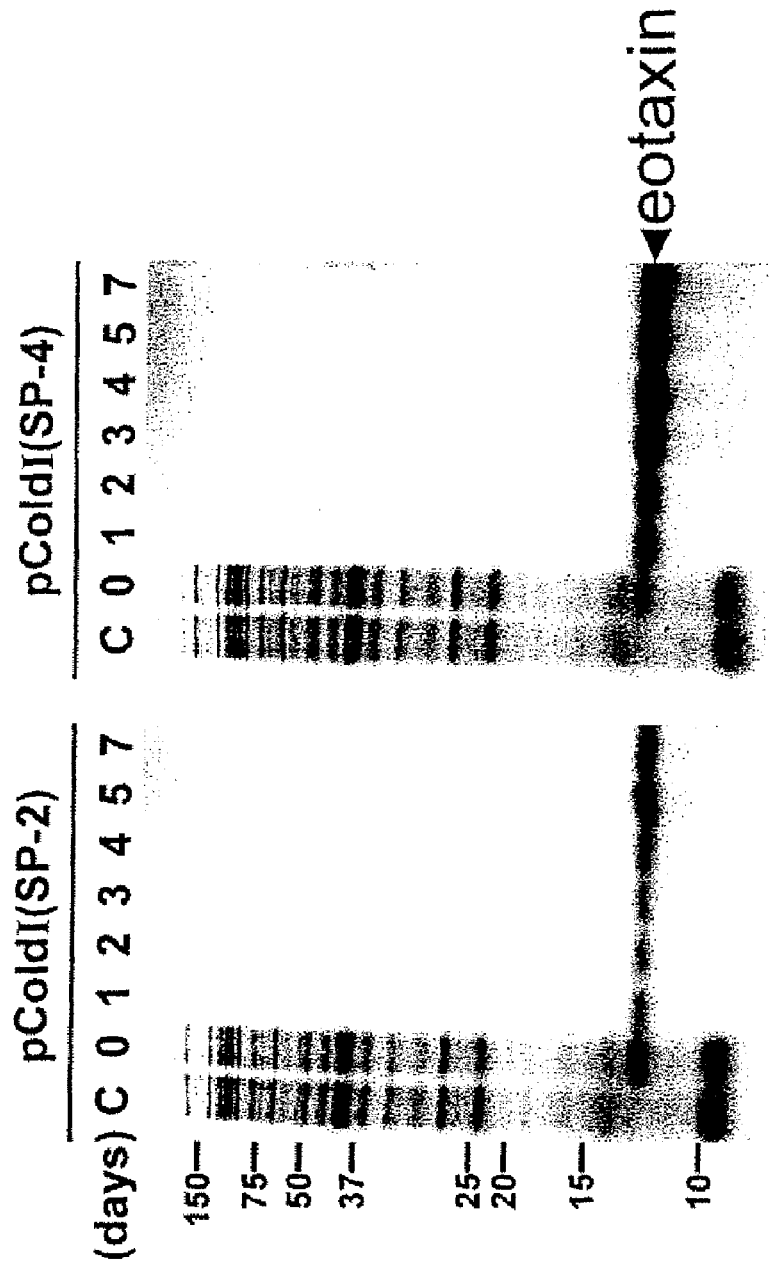
FIG. 6. pColdI(SP-2) and pColdI (SP-4) vectors support sustained, high level target protein expression.
Figure 6B:
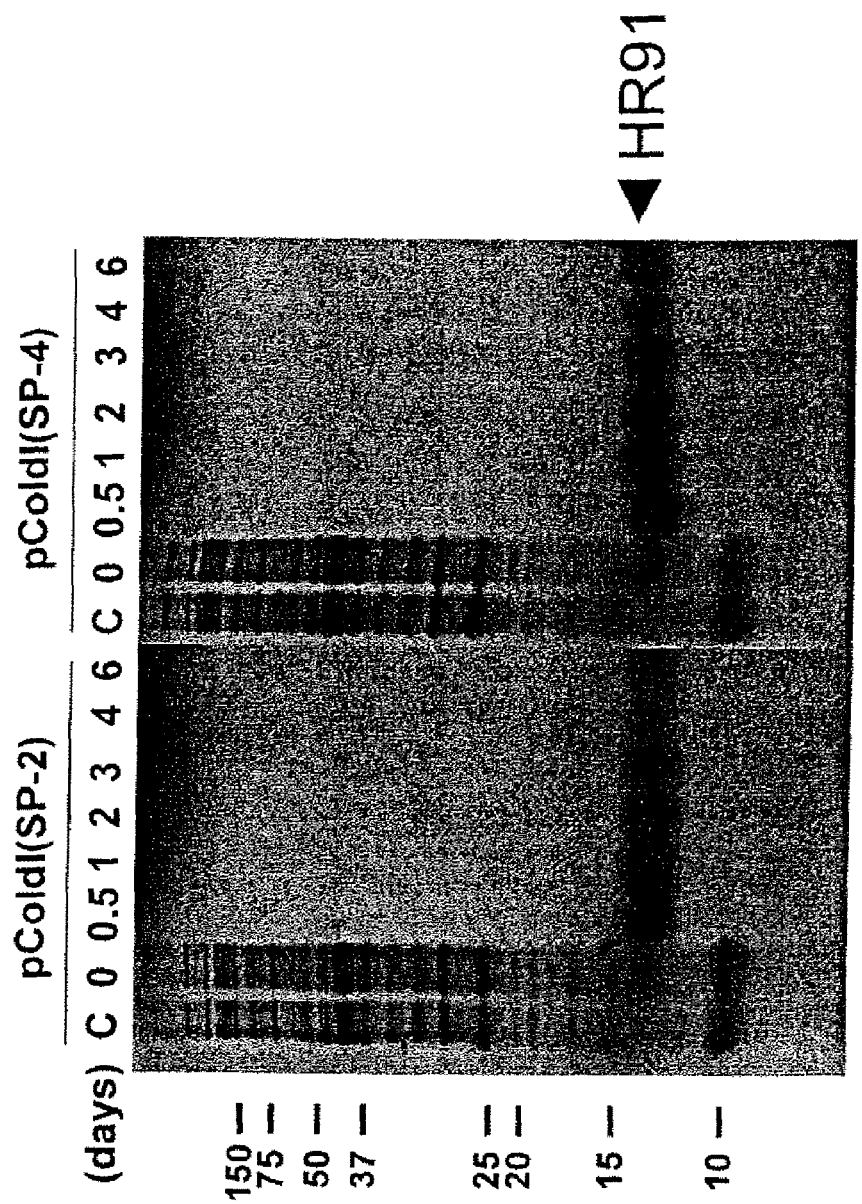
Figure 6C:
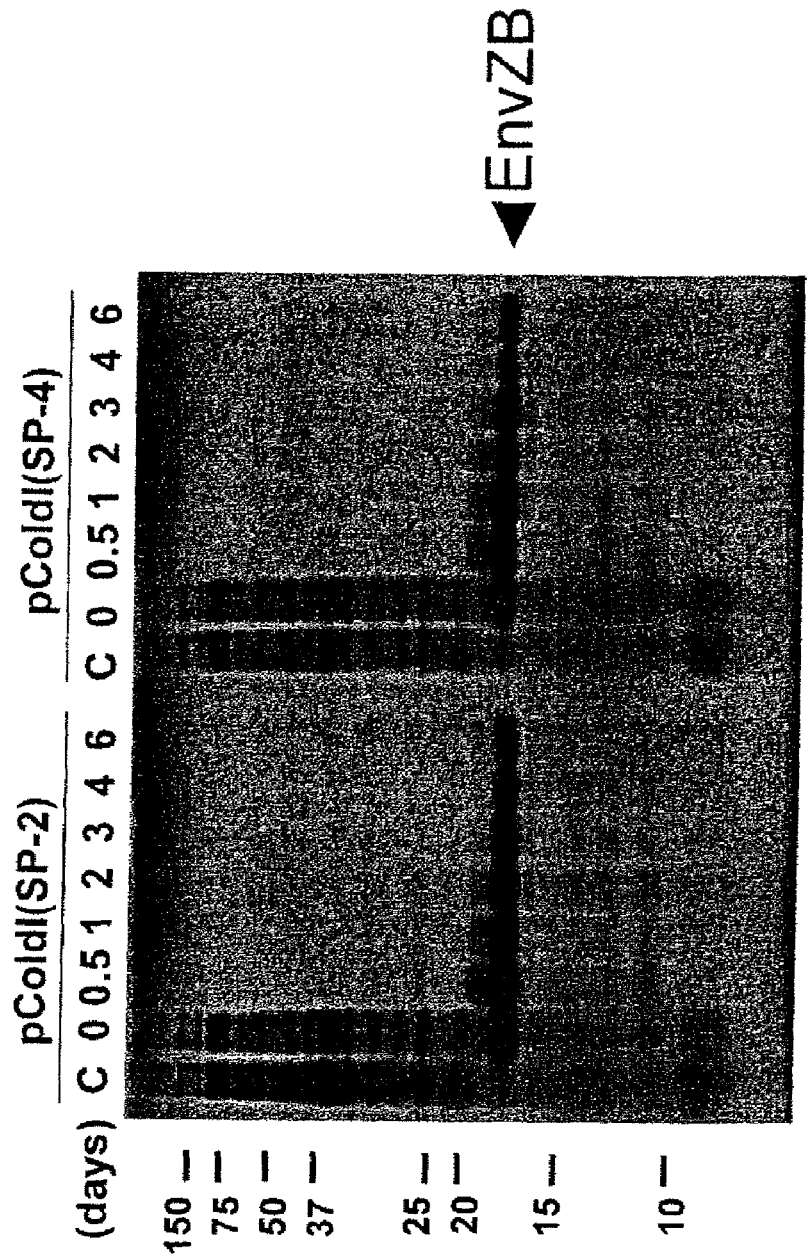
Figure 6D:
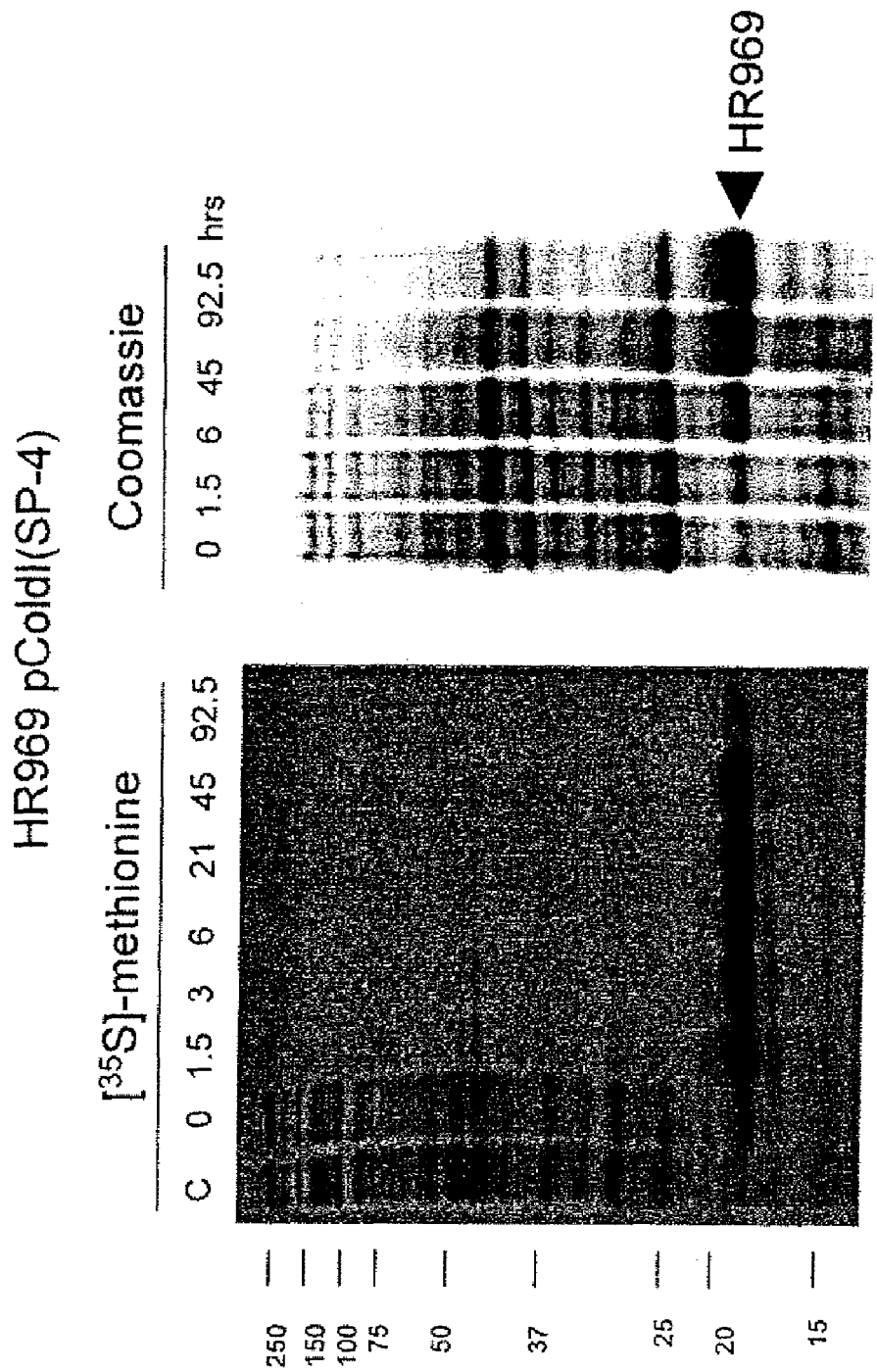

When this gene was expressed with use of pColdI(SP-1) together with pACYCmazF under the same condition as described for FIG. 1, only a low level of eotaxin production was observed for the first 2 hours after which point the production was further reduced to a background level (FIG. 2B, right panel) in comparison with the expression with the ACA-less mRNA (FIG. 2B, left panel).

Curiously, the mazF gene encodes an mRNA that has an unusually high ACA content (9 ACA sequences for a 111 residue protein)—in a dramatic contrast to MazE (82 amino acid residues with only 2 ACA sequences)—suggesting that mazF expression is negatively regulated in cells. Therefore, we constructed the mazF gene with no ACA [pACYCmazF (−9ACA)] and tested whether the removal of these ACA sequences from the mazF coding region may cause more effective reduction of background cellular protein production.

FIG. 3 shows the effect of removal of all ACA sequences in the mazF ORF on eotaxin expression. Panel A shows the amino acid sequence of MazF and the nucleotide sequence of its ORF The triplet sequences underlined (a total of nine) were originally ACA in the wild-type mazF gene, which were changed to MazF-uncleavable sequences. Panel B shows the expression of eotaxin with pColdI(SP-2)eotaxin using the wild-type mazF gene (left panel) and ACA-less mazF gene (right panel). The experiments were carried as described in FIG. 1.

As shown in FIG. 3A (SEQ ID NO: 2 and SEQ ID NO: 4), none of the base substitutions alter the amino acid sequence of MazF. Although cells harboring pYCACmazF(−9ACA) grew a little slower than cells harboring pYCACmazF in M9 medium, the background protein synthesis was further reduced without significant effects on the eotaxin production (FIG. 3B). These results clearly demonstrate that ACA sequences in mRNAs play the crucial role in protein production in MazF-induced cells.

Example 4

Application of the SPP System to Yeast Proteins

We applied the SPP system to two yeast proteins: Hsp10, a heat-shock factor and Rpb12, an RNA polymerase subunit. The ORFs for Hsp10 and Rpb12 contain 3 and 1 ACAs, respectively, which were converted to MazF-uncleavable sequences without altering their amino acid sequences (FIG. 4A). They, together with the wild-type sequences, then were inserted into pColdI(SP-2). The resulting plasmids were termed pColdI(SP-2)Hsp10 for the wild-type Hsp10, pColdI (SP-2)Hsp10(−1ACA) for the mutant Hsp10, pColdI(SP-2) Rpb12 for the wild-type Rpb12 and pColdI(SP-2)Rpb12(−3ACA), respectively. These plasmids were individually transformed into E. coli BL21(DE3) harboring pACYCmazF Protein expression patterns then were examined for 48 hours at 15° C.

The expression of Yeast Proteins in the SPP System is shown in FIG. 4. Using pColdI(SP-2), yeast Hsp10 and Rpb12 were expressed in the SPP system in the presence and the absence of ACA sequences in their genes. Experiments were carried out as described supra for FIG. 1. FIG. 4A shows the expression of Hsp10 using the wild-type and ACA-less Hsp10 genes. The hsp10 ORF consisting of 106 codons contains 3 ACA sequences; GCA-CAA for A25-Q26, ACA for T29 and CCA-CAG for P76-Q77, which were converted to GCC-CAA, ACC and CCC-CAG, respectively (altered bases are in bold). These base substitutions do not alter the amino acid sequence of Hsp10. FIG. 4B shows the expression of Rpb12 using the wild-type and ACA-less genes. The rpb12 ORE consisting of 70 codons contains one ACA for T10, which was converted to ACC for threonine.

FIG. 4A shows that Hsp10 can be expressed with its native 3 ACA sequences (WT) at a reasonably high level. However when all the ACA sequences were removed, Hsp10 synthesis significantly enhanced a few fold. Noticeably, the background was also significantly reduced with the ACA-less Hsp10, likely because more ribosomes were dedicated for the production of Hsp10. FIG. 4B shows that although Rpb12 contains only one ACA, it causes a devastating effect on its production in the SPP system, as little $^{35}$S-methionine incorporation was observed in the WT panel while reasonable incorporation was seen in the ACA-less Rpb12. These results suggest that mRNA sensitivity to MazF may be governed, not only by the number of ACA sequences in an mRNA, but also by effective susceptibility of an ACA sequence to MazF. It is likely that the ACA sequence susceptibility is determined by its location in a single-stranded region of an mRNA as well as the effective translation of an mRNA by ribosomes, as ribosomes are assumed to protect the mRNA from its cleavage by MazF.

Example 5

Application of the SPP System to an Integral Membrane Protein

We attempted to apply the SPP system to a minor integral membrane protein. We chose the gene lspA for signal peptidase II in E. coli, which is specifically required for cleavage of the signal peptides of lipoproteins (Tokuda and Matsuyama, Biochem. Biophys. Acta 1693: 5-13 (2004)). E. coli contains a total of 96 lipoproteins, which are known to assemble either in the inner membrane or in the outer membrane depending upon the nature of the second amino acid residue (acidic or neutral) of the mature lipoproteins (Yamaguchi and Inouye, Cell 53: 423-432 (1988); Tokuda and Matsuyama, Biochem. Biophys. Acta 1693: 5-13 (2004)). The signal peptides of all the other secreted proteins are cleaved by signal peptidase I (leader peptidase), which is estimated to exist only at a level of 500 molecules per cell in E. coli (Wolfe et al., J. Biol. Chem. 257: 7898-7902 (1982)).

Lipoprotein Signal Peptidase (LspA) also is considered to be a very low abundant protein in the inner membrane. It consists of 164 amino acid residues and contains four presumed transmembrane domains, indicating that LspA is an integral inner membrane protein. Three ACA sequences in the lspA ORE were altered to non-MazF-cleavable sequences without changing its amino acid sequence and the ACA-less LspA was expressed using pColdI(SP-2) in the SPP system using mazF(−9ACA).

The expression of LspA, an inner membrane protein in the SPP system using pColdL(SP-2) are shown in FIG. 5. LspA, signal peptidase II or lipoprotein signal peptidase was expressed in the SPP system as described in FIG. 1. Panel A shows total cellular proteins; and Panel B shows the membrane fraction: The position of LspA is shown by an arrow.

As shown in FIG. 5A, the expression of LspA in the SPP system apparently is toxic to the cells, as $^{35}$S-methionine incorporation lasted only 1 hour after IPTG induction. Nevertheless, as shown in FIG. 5B, a reasonable $^{35}$S-methionine incorporation into LspA appears to be achieved as the LspA band densities at 0 and 1 hr time points were the highest comparing them with other cellular protein bands (compare with the C lane in FIG. 5A). The background cellular protein synthesis observed at 0 and 1 hr was easily removed by ultracentrifugation, and $^{35}$S-methionine incorporation was highly enriched in the membrane fraction.

Discussion

The present work demonstrates that complete inhibition of cellular protein synthesis by an mRNA interferase does not cause deteriorating effects on the cellular physiology. As a result of fragmentation of almost all cellular mRNAs by MazF at ACA sequences, cellular protein synthesis is completely blocked, which in turn leads to complete cell growth arrest. However, to our surprise, growth arrested cells by MazF induction were found to be fully capable of synthesizing proteins at a high level for a long period of time (at least 96 hr at 15° C.) if their mRNAs are engineered to have no ACA sequences. In this fashion we have achieved for the first time to establish the single-protein production (SPP) in vivo.

Our results demonstrate that MazF-induced cells are not dead. MazF induction does not hamper cellular integrity maintaining energy metabolism producing enough ATP required various cellular functions including RNA and protein synthesis. In addition biosynthesis of amino acids and nucleotides are also maintained intact. It is quite surprising to find that in the complete absence of new cellular protein synthesis, all the protein factors required for these cellular functions (for example protein factors required for protein synthesis) and cellular metabolisms are stably maintained at least 96 hours at 15° C. It remains to be determined how long these cellular functions could be retained without affecting the SPP capability. Although at a glance they appear to be in a dormant state, they are fully capable of RNA and protein synthesis and distinctly different from the dormancy caused by the stationary phase due to nutritional deprivation. We propose to term the physiological state created by MazF induction "quasi-dormant" state. It remains to be determined if the quasi-dormant cells are dead or undead. Bacterial viability is often determined by the colony forming ability of cells after various treatments. The viability of E. coli cells after MazF induction has been examined in this fashion and shown to be resumed during limited time incubation after MazF induction if MazE is induced (Pedersen et al., Mol. Microbiol. 45: 501-10 (2002); Amitai et al., J. Bacteriol. 186: 8295-8300 (2004)). Therefore, the effect of MazF is reversible to a certain extent, however it has been argued that there is 'a point of no return', from which point all cells are destined to die (Amitai et al., J. Bacteriol. 186: 8295-8300 (2004)). Importantly, the MazE gene used by both group contains two ACA sequence in its ORF. The present results clearly indicate that in order for any genes to be expressed in MazF-induced cells, ACA sequences in these genes have to be converted to MazF-uncleavable sequences. Therefore it is highly possible that the quasi-dormant cells expressing MazF cannot express MazE unless all the ACA sequences are eliminated from its OR.

The ability to produce only a single protein of interest in living cells or undead cells provides a novel approach for studying the various aspects of proteins in living cells previously unattainable. Since by using the SPP system a protein of interest can be exclusively labeled with isotopes ($^{15}$N and $^{13}$C) in living cells, it may be even possible to examine NMR structures of proteins in living cells. Recently we have shown that NMR structural determination of a protein can be achieved using cell lysates without protein purification by expressing a protein of interest by high expression cold-shock vectors, pCold (Qing et al., Nat. Biotechnol. 22: 877-882 (2004)). We now demonstrate that the use of MazF together with pCold vectors dramatically reduces the signal-to-noise ratio as the background cellular protein synthesis can be almost completely blocked by MazF induction. In these experiments we showed that the removal of ACA sequences from pColdI vector itself is also very important by which 5 fold improvement of eotaxin production was observed. When combined with MazF, the rate of eotaxin synthesis was at the level 90% of the total cellular protein synthesis as judged by $^{35}$S-methionine incorporation. The remaining 10% consisted of a general background without incorporation into any specific protein bands. This in turn enables one to perform the structural study of very low abundant proteins, whose production is limited because of their toxicity when expressed in a large quantity. We indeed demonstrated in the present paper that LspA, a very low abundant inner membrane protein, can be exclusively expressed in the membrane fraction. Some proteins may be folded only in living cells, whose structural study may be achieved only by the use of the SPP system.

Another unique advantage of the SPP system is that a protein of interest can be produced or labeled with isotopes in a highly concentrated culture as cell growth is completely blocked upon MazF induction. It is possible that the SPP system can be applied for the production of not only proteins but also other non-protein compounds. Furthermore the SPP system may not be limited only to bacteria, and MazF and other mRNA interferases may be applied for eukaryotic cells to create the SPP systems in yeast and mammalian cells.

Example 6 pColdI(SP-2) and pColdI (SP-4) Vectors Support Sustained, High Level Target Protein Expression All SPP plasmids exploit a pCold vector backbone designed for high yield protein expression under cold shock conditions[3]. pColdI features include a cspA promoter and translation-enhancing element to drive high levels of target protein transcription and translation upon cold shock, a His$_6$ tag sequence, a factor Xa cleavage site and an amino terminal His-Met encoding sequence comprising an Nde I site that enables the in-frame insertion of any target gene. With the goal of enhancing expression levels, a second generation plasmid pColdI(SP-4) was created from the SPP plasmid pColdI(SP-2). The pColdI(SP-2) vector was modified such that all of the ACAs were removed from the relevant 5' sequences1; subsequent removal of a single ACA from the 3' untranslated region (UTR) of pColdI(SP-2) resulted in the pColdI(SP-4) SPP vector.

The efficacy of pColdI(SP-4) relative to its pColdI(SP-2) progenitor in the SPP system was first tested by assessing both the levels and duration of expression of the test protein eotaxin, a 74 amino acid human chemokine (FIG. 1A). New synthesis of eotaxin from either pColdI(SP-2) or pColdI(SP-4) was assessed for up to seven days after its coinduction with MazF by monitoring [$^{35}$S]-methionine incorporation by sodium dodecyl sulfate-polyacrylamide gel electrophoresis (SDS-PAGE) and autoradiography. Eotaxin synthesis rates from pColdI(SP-4) gradually increased from day one to three, peaked between day three and four, and were sustained at that level through the final seven day time point. In contrast, eotaxin expression levels from pColdI(SP-2) were relatively modest initially, increased only marginally, peaked later (day five) and sustained peak expression through the seven day time point. Therefore, pColdI(SP-4) supports higher levels of eotaxin expression, suggesting that removal of ACAs at the 3' UTR of the vector would generally enhance expression levels. In addition, these results demonstrated that quasi-dormant E. coli cells are able to translate proteins for at least seven days despite being growth arrested.

The efficacy of both plasmids was then tested with two additional proteins, EnvZB, the 161 amino acid ATP binding domain of the *E. coli* EnvZ histidine kinase and a 72 amino acid human protein of unknown function designated HR91 by the Northeast Structural Genomics Consortium. In contrast to eotaxin, HR91 (FIG. 1B) and EnvZB (FIG. 1C) expression appeared almost identical in pColdI(SP-2) versus pColdI(SP-4). The expression patterns also differed from eotaxin, they peaked earlier (0.5-1 day) and then gradually decreased through day seven. Therefore, the eotaxin results did not reflect a general trend, instead, the target protein appears to dictate the expression characteristics and protein synthesis rates from either the original pColdI(SP-2) or the modified pColdI(SP-4) SPP vector. However, since synthesis rates of new target proteins are never worse, and sometimes even better using pColdI(SP-4), we have selected this modified vector for the remainder of the SPP expression studies described in this study.

Next, we used another NESG human target protein of unknown function called HR969 (139 amino acids) to compare how target protein synthesis rates relate to the cumulative levels of target protein present in the cell. HR969 protein synthesis rates measured by [$^{35}$S]-methionine incorporation were compared to cellular protein levels assessed by Coomassiae staining (FIG. 1D). The levels of HR969 protein accumulated steadily to the 45 and 92.5 hour time points when peak expression was observed, representing 21% and 24% of the total protein, respectively. We obtained comparable results for both EnvZB and HR91 (data not shown), indicating that the pColdI(SP-4) SPP expression vector supports enhanced, sustained and stable recombinant protein production.

Example 7

SPP Cultures can be Highly Condensed without Significant Reduction in Target Protein Yields Since cell growth is completely inhibited upon MazF induction, we examined if cell cultures could tolerate substantial condensation for protein production by the SPP system without affecting the protein yield. *E. coli* BL21 cultures harboring pACYCmazF and pColdI(SP4)envZB were subjected to normal SPP induction conditions except that the cells were first pelleted and resuspended in medium to achieve cell concentrations 10-, 20-, 30-, 40-, 50- and 100-fold higher than normal inducing conditions ($OD_{600}$ of 0.5, corresponding to approximately $3\times10^8$ cells/ml). The total cellular protein profiles of samples containing equivalent cell numbers were then analyzed by SDS-PAGE followed by Coomassie Blue staining (FIG. 2). Overall, the cells tolerated concentration remarkably well and continued to express and translate high levels of target protein. In fact, after 21 hrs of induction EnvZB represented the most abundant stainable protein in the full range of concentrated cultures we analyzed. Concentration did not reduce protein yield—the amounts of EnvZB produced for the uncondensed sample (~$3\times10^8$ cells/ml) compared to the 40-fold (~$1.2\times10^{10}$ cells/ml) sample were almost identical. Only upon culture condensation of 50-fold or greater was a reduction in EnvZB protein levels observed. Therefore, MazF induced cells in a quasi-dormant state can withstand substantial (40-fold) condensation without a slight reduction in the yield of target protein.

Example 8

Condensed SPP Cultures Incorporate Selenomethionine with High Efficiency and without Toxicity The ability to produce high levels of a single protein in condensed cultures may have applications for structural analysis of proteins by X-ray crystallography or NMR. Heavy atoms are used as phasing centers for multiwavelength anomalous diffraction (MAD) in synchrotron crystallography[4]. Selenium addition to proteins through in vivo[5,6] or in vitro[7] incorporation of precursor selenomethionine is the most common approach to enable MAD phasing. However, in vivo selenomethionine incorporation into *E. coli* proteins is cytotoxic and leads to growth inhibition; the in vitro system is technically difficult to construct in the laboratory and expensive if purchased commercially. Selenomethionine induced cytotoxicity and growth inhibition should not be an issue for the condensed SPP (cSPP) approach since these cells are already growth arrested. More importantly, in cSPP the target protein alone accounts for virtually all of the new protein synthesis so that the other cellular proteins that typically contribute to cytotoxicity upon selenomethionine labeling are virtually absent. therefore, cSPP should offer considerable advantages for the incorporation of selenomethionine, other analogs or isotopes used for structural determination.

Using 40-fold condensed culture conditions (the maximal condensation for highest yield), we assessed whether selenomethionine substitution affected the yield of target protein and also measured the efficacy of selenomethionine replacement into EnvZB (FIG. 3A). The amount of selenomethionine-containing EnvZB (lane 5) was almost identical to that in the control experiment done under the same conditions but without selenomethionine (lane 3), indicating that selenomethionine incorporation did not adversely affect EnvZB protein production in our SPP system. Histidine tagged EnvZB was then purified and the masses of wild type versus selenomethione-substituted EnvZB were analyzed using mass spectroscopy (FIGS. 3B,C). Calculation of mass increase indicated that approximately 90% of the methionines—on average 6.3 of the seven methionine residues (excluding the initiation methionine)—were substituted with selenomethionine.

Example 9

Effective Fluorophenylalanine Substitution without Toxicity Using cSPP

Replacement of phenylalanine residues in a protein with p-fluoro-L-phenylalanine (F-Phe) can be implemented for the structural analysis of the protein by $^{19}$F NMR[8,9]. However, as with selenomethionine substitution, F-Phe substitution is cytotoxic. We followed the expression of the CspA in a manner analogous to that demonstrated for selenomethionine EnvZB. CspA was expressed with pColdI(SP4)cspA for 21 hr with and without the addition of F-Phe (FIG. 4A). The addition of F-Phe did not adversely affect CspA production in the SPP system. We then affinity purified the 86-residue CspA product and used mass spectroscopy to determine the extent of F-Phe substitution (FIGS. 4B,C). Although the endogenous Phe biosynthesis was not inhibited in the present SPP system, substantial incorporation of F-Phe (approximately 60 to 70% of total Phe residues) was observed, indicating that toxic F-Phe can be efficiently incorporated into a protein without affecting its yield.

Example 10 cSPP Cultures Incorporate $^{15}N$ with Very High Efficiency

We have previously demonstrated that the signal-to-noise ratio of [$^{35}S$]methionine labeling of a protein of interest was very high in the SPP system since background protein synthesis is virtually absent[1]. Therefore, the use of the SPP system may be ideal for $^{15}N$ and $^{13}C$ isotope labeling of proteins for NMR structural analysis. To test this, EnvZB was expressed using 20-fold condensed culture containing [$^{15}N$] $NH_4Cl$. A control culture was also prepared in the identical manner except that the medium instead contained [$^{14}N$] $NH_4Cl$. We observed no difference in protein yields between [$^{15}N$] $NH_4Cl$ versus [$^{14}N$] $NH_4Cl$ incorporation experiments (data not shown). Both proteins were then affinity purified and their tryptic peptides were analyzed by mass spectroscopy.

We chose the tryptic peptide YGNGWIK from EnvZB (which contains 10 nitrogen atoms and 40 carbon atoms) for comparative analysis using mass spectroscopy. The control peptide has three distinct masses due to the presence of naturally abundant $^{13}C$ (approximately 1%, FIG. 5A). Of the three peaks, the major peak I contains only $^{14}N$ and $^{12}C$, and peaks II and III contain one and two $^{13}C$ atoms, respectively, in the peptide. Assuming that the peak heights are proportional to the amount of peptide in the peaks, the level of the naturally abundant $^{13}C$ is estimated to be 1.06%. The analysis of the peptide from $^{15}N$-labeled EnvZB shows two distinct peak profiles (FIG. 5B); the peak profile at the left is identical to the pattern in FIG. 5A, indicating that these peaks were derived from EnvZB produced before isotope labeling. This background $^{14}N$-labeled EnvZB is estimated to comprise approximately 20% of the total EnvZB produced under these SPP conditions. Seven major peaks constitute the $^{15}N$-labeled peptides; major peak 5 represents a mixture of the peptide consisting of $9^{15}N$, $1^{14}N$, $0^{13}C$ and $40^{12}C$ and the peptide of $8^{15}N$, $2^{14}N$, $1^{13}C$ and $39^{12}C$. Peak 4 is the mixture of four peptides: peptide one $10^{15}N$, $1^{14}N$, $0^{13}C$ and $40^{12}C$, peptide two $9^{15}N$, $2^{14}N$, $1^{13}C$ and $39^{12}C$, peptide three $9^{15}N$, $1^{14}N$, $0^{13}C$ and $40^{12}C$, peptide four $8^{15}N$, $2^{14}N$, $1^{13}C$ and $39^{12}C$. On the basis of the peak distribution due to the naturally abundant $^{13}C$ (FIG. 5A), peptide one containing $10^{15}N$ represents 6% of the total peptides analyzed; peptide two ($9^{15}N$), 38%; peptide three ($8^{15}N$), 31% and peptide four ($7^{15}N$), 15%. These results demonstrate that ~90% of the peptides produced after the addition of $^{15}N$-$NH_4Cl$ contain at least seven $^{15}N$ atom substitutions out of the ten total nitrogen atoms.

Example 11

Methods

Culture Condensation

E. coli BL21(DE3) transformed with pACYCmazF and pCold(SP4)envZB(-ACA) was grown in 1000 ml of M9-glucose medium at 37° C. When the $OD_{600}$ reached 0.5, the culture was chilled in an ice water bath to quickly reach 15° C. and incubated at 15° C. for 45 min to acclimate the cells to cold shock conditions. Cells were harvested and resuspended in 10 ml of chilled M9-glucose medium containing 1 mM IPTG (100 times concentrated). Five ml of this 100-fold condensed culture was transferred into a 25-ml culture flask. The remaining 5 ml was appropriately diluted with chilled M9 medium containing 1 mM IPTG to make 50-, 40-, 30-, 20-, 10- and 1-fold condensed cultures. Each culture was transferred into a 25-ml culture flask and incubated in a water bath shaker at 15° C. for 21 additional hr to induce both MazF and EnvZB. Cells were collected by centrifugation and resuspended such that each sample comprised an extract from an equal number of cells/ml and equal volumes were loaded and subjected to SDS-PAGE followed by Coomassie Blue staining.

Incorporation of Amino Acid Analogs

EnvZB and CspA were expressed in order to demonstrate the efficiency of incorporation of selenomethionine and F-Phe, respectively. For selenomethionine incorporation, E. coli BL21(DE3) transformed with both pACYCmazF and pCold(SP-4)envZB(-ACA) was grown in 200 ml of M9-glucose medium at 37° C. When the $OD_{600}$ reached 0.5, the culture was shifted to 15° C. for 45 min to acclimate the cells to cold shock conditions. Cells were harvested and suspended with 5 ml of M9-glucose medium containing Lys (100 µg/ml), Phe (100 µg/ml), Thr (100 µg/ml), Ile (50 µg/ml), Leu (50 µg/ml) and Val (50 µg/ml) (40-times concentrated culture). Cultures were incubated at 15° C. for 15 min to inhibit endogenous methionine biosynthesis and then 25 µl of 12 mg/ml seleno-L-methionine (the final concentration of 60 µg/ml) and 5 µl of 1 M IPTG (the final concentration of 1 mM) was added to the culture. Both CspA and EnvZB were expressed at 15° C. for 21 hr. For the incorporation of F-Phe, 50 µl of 6 mg/ml F-Phe was added immediately after concentrating. In contrast to selenomethionine labeling conditions, phenylalanine biosynthesis was not prevented during F-Phe incorporation.

Incorporation of $^{15}N$

E. coli BL21(DE3) transformed with pACYCmazF and pCold(SP-4)envZB(-ACA) was grown in 1000 ml of M9-glucose medium at 37° C., When the $OD_{600}$ reached 0.5, the culture was shifted to 15° C. for 45 min to acclimate the cells to cold shock conditions. 1 mM IPTG was added to induce expression of both MazF and EnvZB followed by a 15° C. for 3 hr incubation at to eliminate isotope incorporation into background cellular proteins. Cells were harvested and resuspended with 50 ml of $^{15}N$-M9-glucose medium (1 g $^{15}NH_4Cl/l$) containing 1 mM IPTG (20-times concentrated culture). EnvZB was expressed at 15° C. for 15 hr.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. Suzuki, M., Zhang, J., Liu, M., Woychik, N. A. & Inouye, M. Single protein production in living cells facilitated by an mRNA interferase. Mol Cell 18, 253-261 (2005).
2. Zhang, Y. et al. MazF cleaves cellular mRNAs specifically at ACA to block protein synthesis in Escherichia coli. Mol Cell 12, 913-923 (2003).
3. Qing, G. et al. Cold-shock induced high-yield protein production in Escherichia coli. Nat Biotechnol 22, 877-882 (2004).
4. Hendrickson, W. A. Synchrotron crystallography. Trends Biochem Sci 25, 637-643 (2000).
5. Bellizzi, J. J., Widom, J., Kemp, C. W. & Clardy, J. Producing selenomethionine-labeled proteins with a baculovirus expression vector system. Structure 7, R263-267 (1999).
6. Hendrickson, W. A., Horton, J. R. & LeMaster, D. M. Selenomethionyl proteins produced for analysis by multiwavelength anomalous diffraction (MAD): a vehicle for direct determination of three-dimensional structure. Embo J 9, 1665-1672 (1990).
7. Kigawa, T. et al. Selenomethionine incorporation into a protein by cell-free synthesis. J Struct Funct Genomics 2, 29-35 (2002).
8. Bourret, R. B., Drake, S. K., Chervitz, S. A., Simon, M. I. & Falke, J. J. Activation of the phosphosignaling protein CheY. II. Analysis of activated mutants by 19F NMR and protein engineering. J Biol Chem 268, 13089-13096 (1993).
9. Drake, S. K., Bourret, R. B., Luck, L. A., Simon, M. I. & Falke, J. J. Activation of the phosphosignaling protein CheY. I. Analysis of the phosphorylated conformation by 19F NMR and protein engineering. J Biol Chem 268, 13081-13088 (1993).
10. Tian, J. et al. Accurate multiplex gene synthesis from programmable DNA microchips. Nature 432, 1050-1054 (2004).
11. Dedmon, M. M., Patel, C. N., Young, G. B. & Pielak, G. J. FlgM gains structure in living cells. Proc Natl Acad Sci USA 99, 12681-12684 (2002).
12. Serber, Z. et al. High-resolution macromolecular NMR spectroscopy inside living cells. J Am Chem Soc 123, 2446-2447 (2001).
13. Serber, Z., Ledwidge, R., Miller, S. M. & Dotsch, V. Evaluation of parameters critical to observing proteins inside living Escherichia coli by in-cell NMR spectroscopy. J Am Chem Soc 123, 8895-8901 (2001).

What is claimed is:

1. A system for expressing a single target protein in a transformable living cell while reducing non-target cellular protein synthesis, comprising
   (a) an isolated transformable living cell comprising cellular mRNA having at least one first MazF recognition sequence;
   (b) a first expression vector comprising an isolated nucleic acid sequence encoding MazF polypeptide, wherein the isolated nucleic acid sequence encoding the MazF polypeptide is mutated by replacing at least one second MazF recognition sequence with an alternate triplet codon sequence to produce a mutated nucleic acid sequence encoding an amino acid sequence identical to the amino acid sequence of a nonmutated MazF polypeptide;
   (c) optionally, a second expression vector comprising an isolated nucleic acid sequence encoding a target protein, wherein the isolated nucleic acid sequence encoding the target protein is mutated by replacing at least one third MazF recognition sequence with an alternate triplet codon sequence to produce a mutated nucleic acid sequence encoding an amino acid sequence identical to the amino acid sequence of a nonmutated target protein;

wherein the isolated cell is transformed with the first expression vector and the second expression vector; and wherein the isolated cell is maintained under conditions permitting expression of the mutant target protein in the cell.

2. The system according to claim 1, wherein the first and second expression vectors each further comprise at least one regulatory sequence.

3. The system according to claim 2, wherein the at least one regulatory sequence is at least one inducible promoter.

4. The system according to claim 1, wherein cellular messenger RNA is selectively cleaved by the MazF polypeptide thereby reducing nontarget cellular protein synthesis.

5. The system according to claim 1, wherein the first MazF recognition sequence, the second MazF recognition sequence, and the third MazF recognition sequence are the same MazF recognition sequence.

6. The system according to claim 5, wherein the MazF recognition sequence is adenine-cytosine-adenine.

7. The system according to claim 1, wherein an expressed messenger RNA encoding the mutated target protein is stably maintained in the cell.

* * * * *

SEQUENCE LISTING

```
<160> NUMBER OF SEQ ID NOS: 4

<210> SEQ ID NO 1
<211> LENGTH: 276
<212> TYPE: DNA
<213> ORGANISM: Artificial Sequence
<220> FEATURE:
<223> OTHER INFORMATION: Human eotaxin gene designed using preferred E.
      coli codons

<400> SEQUENCE: 1
augaaucaua aagugcauca ucaucaucau cauaucgaag guaggcauau ggguccagca      60
ucuguuccga cuaccuguug cuuuaaccug gcgaaccgca aaauuccgcu gcagcgccug    120
gaaagcuauc gccguauuac cucuggcaaa ugcccgcaga aagcggugau cuuuaaaacc    180
aaacuggcga agauauuug cgcggauccg aaaaaaaaau ggguugcagga uucuaugaaa    240 uaucuggauc agaaaucucc gaccccgaaa ccguaa                              276

<210> SEQ ID NO 2
<211> LENGTH: 336
<212> TYPE: RNA
<213> ORGANISM: Artificial Sequence
<220> FEATURE:
<223> OTHER INFORMATION: ACA-less MazF ORF

<400> SEQUENCE: 2
augguaagcc gauacguacc cgauaugggc gaucugauuu ggguugauuu ugacccgacc      60
aaagguagcg agcaagcugg ccaucgucca gcuguuguuc ugaguccuuu cauguauaau    120
aauaaaaccg guaugugucu gugugguccu uguaccacgc aaucaaaagg auauccguuc    180
gaaguuguuu uauccgguca ggaacgugau ggcguagcgu uagcugauca gguaaaaagu    240
```

```
aucgccuggc gggcaagagg agcaacgaag aaaggaaccg uugccccaga ggaacugcaa      300
cucauuaaag ccaaaauuaa cguacugauu ggguag                                336
```

```
<210> SEQ ID NO 3
<211> LENGTH: 91
<212> TYPE: PRT
<213> ORGANISM: Artificial Sequence
<220> FEATURE:
<223> OTHER INFORMATION: Amino acid sequence encoded by a human eotaxin
      gene designed using preferred E. coli codons

<400> SEQUENCE: 3

Met Asn His Lys Val His His His His His Ile Glu Gly Arg His
1               5                   10                  15

Met Gly Pro Ala Ser Val Pro Thr Thr Cys Cys Phe Asn Leu Ala Asn
                20                  25                  30

Arg Lys Ile Pro Leu Gln Arg Leu Glu Ser Tyr Arg Arg Ile Thr Ser
            35                  40                  45

Gly Lys Cys Pro Gln Lys Ala Val Ile Phe Lys Thr Lys Leu Ala Lys
        50                  55                  60

Asp Ile Cys Ala Asp Pro Lys Lys Lys Trp Val Gln Asp Ser Met Lys
65                  70                  75                  80

Tyr Leu Asp Gln Lys Ser Pro Thr Pro Lys Pro
                85                  90

<210> SEQ ID NO 4
<211> LENGTH: 111
<212> TYPE: PRT
<213> ORGANISM: Artificial Sequence
<220> FEATURE:
<223> OTHER INFORMATION: Amino acid sequence encoded by an ACA-less MazF
      ORF

<400> SEQUENCE: 4

Met Val Ser Arg Tyr Val Pro Asp Met Gly Asp Leu Ile Trp Val Asp
1               5                   10                  15

Phe Asp Pro Thr Lys Gly Ser Glu Gln Ala Gly His Arg Pro Ala Val
                20                  25                  30

Val Leu Ser Pro Phe Met Tyr Asn Asn Lys Thr Gly Met Cys Leu Cys
            35                  40                  45

Val Pro Cys Thr Thr Gln Ser Lys Gly Tyr Pro Phe Glu Val Val Leu
        50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
                100                 105                 110
```